(12) United States Patent
Igawa et al.

(10) Patent No.: US 10,310,350 B2
(45) Date of Patent: Jun. 4, 2019

(54) ORGANIC COMPOUND, ELECTROCHROMIC COMPOUND, AND ELECTROCHROMIC ELEMENT, OPTICAL FILTER, LENS UNIT, IMAGING DEVICE, AND WINDOW COMPONENT HAVING SAME

(71) Applicant: CANON KABUSHIKI KAISHA, Tokyo (JP)

(72) Inventors: Satoshi Igawa, Fujisawa (JP); Jun Yamamoto, Tokyo (JP); Kenji Yamada, Yokohama (JP); Tetsuya Tamura, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 73 days.

(21) Appl. No.: 15/591,832

(22) Filed: May 10, 2017

(65) Prior Publication Data

US 2017/0329195 A1   Nov. 16, 2017

(30) Foreign Application Priority Data

May 12, 2016 (JP) .................................. 2016-096254
Apr. 6, 2017 (JP) .................................. 2017-076185

(51) Int. Cl.
*C09K 9/02* (2006.01)
*G02F 1/15* (2019.01)
(Continued)

(52) U.S. Cl.
CPC .............. *G02F 1/15* (2013.01); *C07C 311/48* (2013.01); *C07D 213/22* (2013.01);
(Continued)

(58) Field of Classification Search
CPC ... C07C 311/48; C07D 213/22; C07D 213/65; C07F 9/65583; C09K 9/02; G02F 1/157
(Continued)

(56) References Cited

U.S. PATENT DOCUMENTS

| | | | | |
|---|---|---|---|---|
| 2008/0316574 A1* | 12/2008 | Baumann | ............... | C09K 11/06 359/273 |
| 2017/0329195 A1* | 11/2017 | Igawa | ................. | C07F 9/65583 |
| 2018/0237393 A1* | 8/2018 | Tamura | ................ | C07D 213/06 |

FOREIGN PATENT DOCUMENTS

| | | | |
|---|---|---|---|
| CN | 103059831 | * | 4/2013 |
| JP | 61-148162 A | | 7/1986 |
| WO | WO2017005824 | * | 1/2017 |

OTHER PUBLICATIONS

Miles; Proc. SPIE, 1990, vol. 1323, 200-209. (Year: 1990).*
(Continued)

*Primary Examiner* — Daniel R Carcanague
(74) *Attorney, Agent, or Firm* — Canon U.S.A. Inc., IP Division

(57) ABSTRACT

An organic compound represented by General Formula (1), $$X_1-N^+ \underset{A_1^-}{\bigcirc}\overset{R_1}{-}\underset{A_2^-}{\bigcirc}N^+-X_2 \quad (1)$$

in which, in General Formula (1), $R_1$ represents an alkyl group or an alkoxy group, $X_1$ and $X_2$ are each independently selected from an alkyl group which may have a substituent, an aryl group which may have a substituent, or an aralkyl group which may have a substituent, and $A_1^-$ and $A_2^-$ each independently represent a monovalent anion.

18 Claims, 6 Drawing Sheets

(51) Int. Cl.
  *G02F 1/157* (2006.01)
  *C07C 311/48* (2006.01)
  *C07D 213/22* (2006.01)
  *C07D 213/65* (2006.01)
  *C07F 9/6558* (2006.01)

(52) U.S. Cl.
  CPC ........ *C07D 213/65* (2013.01); *C07F 9/65583* (2013.01); *C09K 9/02* (2013.01); *G02F 1/157* (2013.01); *C09K 2211/1007* (2013.01); *C09K 2211/1014* (2013.01); *C09K 2211/1022* (2013.01); *C09K 2211/1044* (2013.01); *G02F 1/1521* (2013.01); *G02F 2001/151* (2013.01); *G02F 2001/1502* (2013.01)

(58) Field of Classification Search
  USPC ........................................................ 546/257
  See application file for complete search history.

(56) References Cited

OTHER PUBLICATIONS

Barltrop; J. Chem. Soc. Perkin Trans. II 1984, 367-371. (Year: 1984).*

Kamogawa; Bull. Chem. Soc. Jpn. 1985, 58, 2443-2444. (Year: 1985).*

* cited by examiner

ORGANIC COMPOUND, ELECTROCHROMIC COMPOUND, AND ELECTROCHROMIC ELEMENT, OPTICAL FILTER, LENS UNIT, IMAGING DEVICE, AND WINDOW COMPONENT HAVING SAME

BACKGROUND

Field of the Disclosure

The present disclosure relates to an organic compound, an electrochromic compound, and an electrochromic element, an optical filter, a lens unit, an imaging device, and a window component having the same.

Description of the Related Art

An electrochromic element (EC element) is an element having a pair of electrodes and an electrochromic layer (EC layer) disposed between the pair of electrodes. By applying a voltage to the pair of electrodes, the amount of light passing through an EC layer can be adjusted.

For such an EC element, an electrochromic compound (EC compound) having an electrochromic property (EC property) has been used in which the optical absorption properties (coloration state and light transmittance) of a substance change clue to reversible progress of an electrochemical redox reaction. Examples of low molecular weight organic EC compounds include a viologen derivative which is a cathodic EC compound colored by reduction, a phenazine derivative which is an anodic EC compound colored by oxidation, and the like.

The EC element has been applied to a light control mirror of automobiles, electronic paper, and the like using the EC compounds. The devices utilize the property that the display of various color tones can be achieved by selecting the EC compound. In utilizing the EC element, a development of materials of various color tones has suggested the possibility of wide use thereof.

Japanese Patent Laid-Open No. 61-148162 describes a viologen derivative in which an alkyl group is introduced into carbon atoms of at least one of two pyridyl groups forming 4,4'-bipyridinium. Japanese Patent Laid-open No. 61-148162 describes a viologen derivative in which alkyl groups are bonded to the 2,2' sites of the 4,4'-bipyridinium and a viologen derivative in which alkyl groups are bonded to the 3,3' sites of the 4,4'-bipyridinium as specific examples.

However, the wavelength of the absorption peak in a colored state of the viologen derivative in which alkyl groups are bonded to the 2,2' sites of 4,4'-bipyridinium described in Japanese Patent Laid-Open No. 61-148162 has been almost the same as that of viologen not having a substituent in carbon atoms of 4,4'-bipyridinium. In the viologen derivative in which alkyl groups are bonded to the 3,3' sites of 4,4'-bipyridinium, the wavelength of the absorption peak appears in a long wavelength band but the redox reaction does not reversibly progress, and the derivative does not have the EC property.

SUMMARY

In view of the above-described problems, embodiments described below provide an organic compound which has the absorption peak in a long wavelength band as compared with that of viologen in which no substituents are introduced into carbon atoms of 4,4'-bipyridinium in a colored state and in which an electrochemical redox reaction reversibly progresses.

An organic compound according to one aspect of the present disclosure is represented by the following general formula (1),

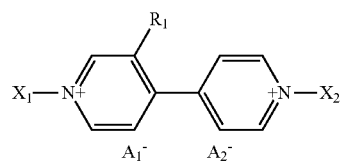

in which, in General Formula (1), $R_1$ represents an alkyl group or an alkoxy group, $X_1$ and $X_2$ are each independently selected from an alkyl group which may have a substituent, an aryl group which may have a substituent, or an aralkyl group which may have a substituent, and $A_1^-$ and $A_2^-$ each independently represent a monovalent anion.

Further features of the present disclosure will become apparent from the following description of exemplary embodiments with reference to the attached drawings.

DESCRIPTION OF THE EMBODIMENTS

Figure 1:
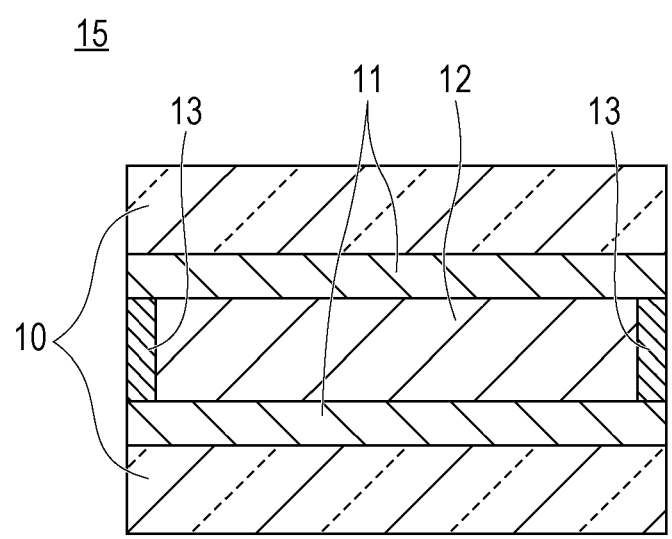
FIG. 1 is a cross-sectional frame format explaining an example of the configuration of an electrochromic element according to an embodiment of the subject application.

An organic compound of the present disclosure is an organic compound having an electrochromic property (EC property). The EC property is a property in which the optical absorption properties (coloration state and light transmittance) of a substance change due to reversible progress of an electrochemical redox reaction, so that the color tone changes. In this embodiment, the coloring means that the transmittance at a specific wavelength decreases. In the following description, the organic compound having the EC property is also referred to as an electrochromic compound (EC compound).

The organic compound according to the present disclosure is an electrochromic compound represented by the following general formula (1).

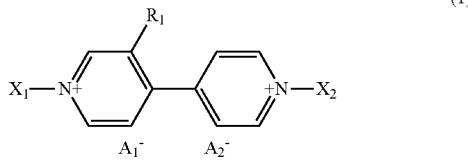

In General Formula (1), $R_1$ represents an alkyl group or an alkoxy group. $X_1$ and $X_2$ each are independently selected from an alkyl group which may have a substituent, an aryl group which may have a substituent, or an aralkyl group which may have a substituent. $A_1^-$ and $A_2^-$ each independently represent a monovalent anion.

The alkyl group represented by $R_1$ may have a linear, branched, or cyclic shape. The alkyl group represented by $R_1$ suitably has 1 or more and 8 or less carbon atoms and more suitably has a linear shape having 1 or more and 8 or less carbon atoms. Specifically, examples of the alkyl group represented by $R_1$ include a methyl group, an ethyl group, a normal propyl group, an isopropyl group, a normal butyl group, a tertiary butyl group, an octyl group, a cyclohexyl group, a trifluoromethyl group, and the like.

The alkoxy group represented by $R_1$ may have a linear, branched, or cyclic shape. The alkoxy group represented by $R_1$ suitably has 1 or more and 8 or less carbon atoms and more suitably has a linear shape having 1 or more and 8 or less carbon atoms. Specifically, examples of the alkoxy group represented by $R_1$ include a methoxy group, an ethoxy group, a normal propyloxy group, an isopropyloxy group, a tartiary butyloxy group, an octyloxy group, a cyclohexyloxy group, a trifluoromethyloxy group, and the like. A hydrogen atom of the alkoxy group may be replaced by a halogen atom.

The alkyl groups which may have a substituent represented by $X_1$ and $X_2$ may have 1 or more and 8 or less carbon atoms and may have a linear, branched, or cyclic shape. Specifically, examples of the alkyl groups represented by $X_1$ and $X_2$ include a methyl group, an ethyl group, a normal propyl group, an isopropyl group, a normal butyl group, a tertiary butyl group, an octyl group, a cyclohexyl group, a trifluoromethyl group, and the like.

The hydrogen atom of the alkyl groups represented by $X_1$ and $X_2$ may be replaced by a fluorine atom. The carbon atom of the alkyl groups represented by $X_1$ and $X_2$ may be replaced by an ester group or a cyano group.

The terminal of the alkyl groups represented by $X_1$ and $X_2$ may have an adsorption group or an acid ester group thereof for adsorption to a porous electrode. Specific examples of the adsorption group or the acid ester group thereof include a carboxyl group and a carboxyl ester group, a sulfonic acid group and a sulfonic acid ester group, a phosphonic acid group and a phosphonic acid ester group, a trialkoxysilyl group, and the like. Furthermore, in order to improve the solubility in an organic solvent, the terminal of the alkyl groups may have ionic groups, such as pyridinium and quinolinium.

Specifically, examples of the aryl groups which may have a substituent represented by $X_1$ and $X_2$ include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, a perylenyl group, and the like.

When the aryl groups represented by $X_1$ and $X_2$ have a substituent, the aryl groups may have at least any one of a halogen atom, an alkyl group having 1 or more and 8 or less carbon atoms, or an alkoxy group having 1 or more and 8 or less carbon atoms as the substituent. The hydrogen atom of the alkyl groups or the alkoxy groups as the substituent of the aryl groups represented by $X_1$ and $X_2$ may be replaced by a fluorine atom.

In the aryl groups which may have a substituent represented by $X_1$ and $X_2$, the terminal of the alkyl group of the substituent may have an adsorption group or an acid ester group thereof for adsorption to a porous electrode. Specific examples of the adsorption group or the acid ester-group thereof include a carboxyl group and a carboxyl ester-group, a sulfonic acid group and a sulfonic acid ester group, a phosphonic acid group and a phosphonic acid ester-group, a trialkoxy silyl group, and the like. Furthermore, in order to improve the solubility in an organic solvent, the terminal of the alkyl group may have ionic groups, such as pyridinium and quinolinium.

Specifically, examples of the aralkyl groups which may have a substituent represented by $X_1$ and $X_2$ include a benzyl group, a phenethyl group, and the like. In General Formula (1), the case where $X_1$ and $X_2$ are aralkyl groups refers to the fact that the aryl group of the aralkyl group is bonded to nitrogen atoms of 4,4'-bipyridinium through the alkyl group. When the aralkyl groups represented by $X_1$ and $X_2$ have a substituent, the aralkyl groups may have an alkyl group having 1 or more and 8 or less carbon atoms or an alkoxy group having 1 or more and 8 or less carbon atoms as the substituent.

From the viewpoint of the radical stability of the organic compound, $X_1$ and $X_2$ are more suitably alkyl groups which may have a substituent or aryl groups which may have a substituent.

$A_1^-$ and $A_2^-$ may be the same or different from each other, and are selected from anions, such as $PF_6^-$, $ClO_4^-$, $BF_4^-$, $AsF_6^-$, $SbF_6^-$, $CF_3SO_3^-$, and $(CF_3SO_2)_2N^-$, and halogen anions, such as $Br^-$, $Cl^-$, and $I^-$. Any one of $PF_6^-$, $ClO_4^-$, $BF_4^-$, $CF_3SO_3^-$, and $(CF_3SO_2)_2N^-$ is suitable. It is more suitable that $A_1^-$ and $A_2^-$ be the same anions.

Since the organic compound according to the present disclosure has the structure represented by General Formula (1), the compound exhibits high transparency when dissolved in a solvent.

The organic compound represented by General Formula (1) is a cathodic EC compound which is colored by reduction. More specifically, the organic compound represented by General Formula (1) is a compound in which an electrochemical redox reaction reversibly progresses, and the optical absorption properties (coloration state and light transmittance) change by a redox reaction.

The organic compound represented by General Formula (1) has the absorption peak in a long wavelength band in a reduced state (colored state) as compared with that of viologen not having a substituent in the carbon atoms of 4,4'-bipyridinium.

Herein, the "absorption peak" in this specification is defined as follows. In the absorption spectrum of the organic compound, the absorbance reaches the maximum and the half bandwidth thereof is 20 nm or more in a certain wavelength band. The half bandwidth is the width of the wavelength in which the absorbance in the absorption spectrum, reaches a half value (half width) of the absorbance at the maximum value. In the absorption peak satisfying the above-described conditions, the wavelength of the absorption peak is a wavelength at which the absorbance reaches the maximum.

It is suitable for the organic compound represented by General Formula (1) to have the absorption peak in a wavelength band of 630 nm or more and 750 nm or less in a colored state. More suitably, the organic compound represented by General Formula (1) has the absorption peak in a wavelength band of 650 nm or more and 750 nm or less in a colored state. This is considered to be because the planarity of the compound in a colored state is different from that of viologen not having a substituent by introducing the alkyl group or the alkoxy group represented by $R_1$ to the third site of 4,4'-bipyridinium. By introducing the alkyl group or the alkoxy group into the third site of one pyridine of 4,4'-bipyridinium, the planarity improves in a colored state, and, as a result, the absorption peak, appears on a long wavelength side.

Thus, according to the organic compound of this embodiment, an organic compound which has the absorption peak in a long wavelength band in a colored state and in which a redox reaction reversibly progresses can be provided.

The organic compound represented by General Formula (1) has high radical stability in a reduced state and has high durable stability in a redox cycle. Therefore, when the organic compound represented by General Formula (1) is used for an electrochromic element (EC element), an EC element having high durable stability can be obtained. Among the organic compounds represented by General Formula (1), an organic compound in which $X_1$ and $X_2$ are alkyl groups which may have a substituent or aryl groups which may have a substituent has radical stability higher than that of an organic compound in which $X_1$ and $X_2$ are aralkyl groups.

A method for producing the organic compound represented by General Formula (1) is not particularly limited and can be produced by a method described below, for example.

In the organic compound represented by General Formula (1), when $X_1$ and $X_2$ are alkyl groups or aralkyl groups, an organic compound (intermediate 1) represented by the following general formula (2) and a halide are first caused to react in a predetermined solvent. The solvent to be used herein is not particularly limited and polar solvents, such as acetonitrile and N,N-dimethyl formamide, are suitably used. Thereafter, an anion exchange reaction is performed with a salt containing a desired anion in a predetermined solvent, whereby the organic compound can be obtained. As the solvent to be used herein, a solvent capable of dissolving both a halogen substance and the salt containing a desired anion is suitably used.

When $X_1$ and $X_2$ are aryl groups, the organic compound represented by General Formula (1) can be obtained by causing a reaction with 2,4-dinitrophenyl halide, causing a reaction with aryl amine, and then performing an anion exchange reaction with a salt containing an anion in a predetermined solvent. Only one imine can also be caused to react by selecting the solvent and the reaction temperature. By repeating the reactions, it is also possible to introduce substituents different from each other into two imines.

Intermediate 1

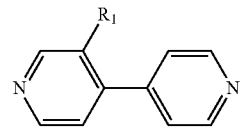

(2)

A method for producing the intermediate 1 is not particularly limited and the intermediate 1 can be produced by a method described below, for example. An example of a synthetic route of the intermediate 1 is described below.

In the synthetic route of the intermediate 1, $R_1$ represents the same substituent as that of General Formula (1) and X represents a halogen atom. The intermediate 1 can be synthesized by a coupling reaction of 4-halogenated pyridine having an alkyl group or an alkoxy group at the third site and 4-pyridyl boronic acid.

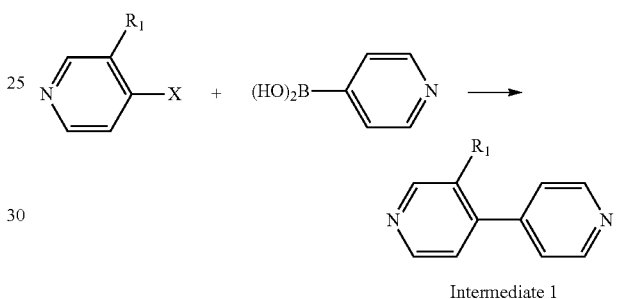

Intermediate 1

A specific structural formula of the organic compound represented by General Formula (1) is shown below. However, the organic compound represented by General Formula (1) according to the present disclosure is not limited thereto.

Among organic compounds shown below as examples, Group A is an example of organic compounds when $R_1$ is an alkyl group which may have a substituent and $X_1$ and $X_2$ are alkyl groups which may have a substituent in General Formula (1). Group B is an example of organic compounds when $R_1$ is an alkyl group which may have a substituent and $X_1$ and $X_2$ are aryl groups which may have a substituent in General Formula (1). Group C is an example of organic compounds when $R_1$ is an alkyl group which may have a substituent and $X_1$ and $X_2$ are different from each other in General Formula (1). Group D is an example of organic compounds when $R_1$ is an alkyl group which may have a substituent and $X_1$ and $X_2$ are aralkyl groups which may have a substituent in General Formula (1). Group E is an example of organic compounds when $R_1$ is an alkoxy group which may have a substituent and $X_1$ and $X_2$ are alkyl groups which may have a substituent in General Formula (1). Group F is an example of organic compounds when $R_1$ is an alkoxy group which may have a substituent and $X_1$ and $X_2$ are aryl groups which may have a substituent in General Formula (1). Group G is an example of organic compounds when $R_1$ is an alkoxy group which may have a substituent and $X_1$ and $X_2$ are different from, each other in General Formula (1). Group H is an example of organic, compounds when $R_1$ is an alkoxy group which may have a substituent and $X_1$ and $X_2$ are aralkyl groups which may have a substituent in General Formula (1).

A-1
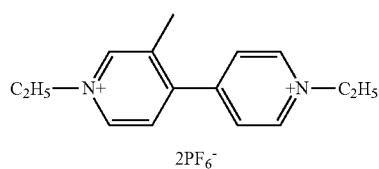
2PF$_6^-$
A-2
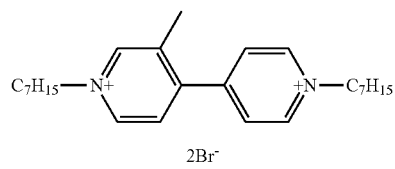
2Br$^-$
A-3
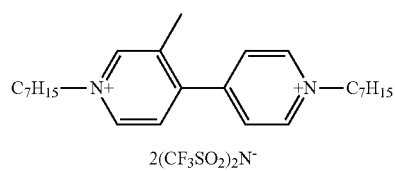
2(CF$_3$SO$_2$)$_2$N$^-$
A-4
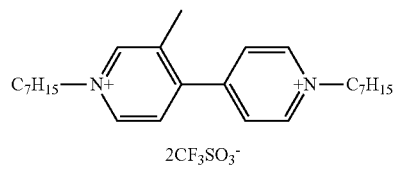
2CF$_3$SO$_3^-$
A-5
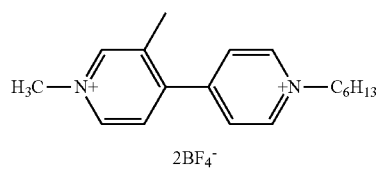
2BF$_4^-$
A-6
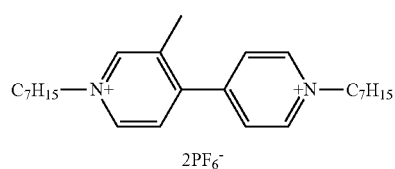
2PF$_6^-$
A-7
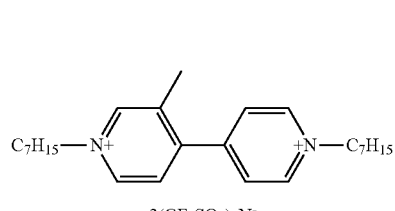
2(CF$_3$SO$_2$)$_2$N$^-$
A-8
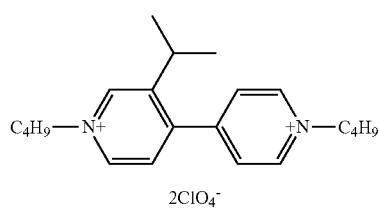
2ClO$_4^-$
-continued
A-9
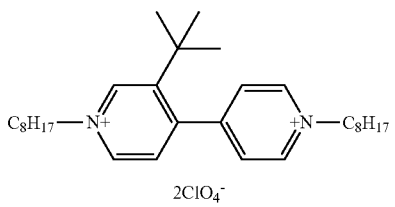
2ClO$_4^-$
A-10
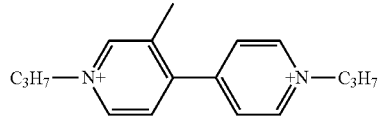
2I$^-$
B-1
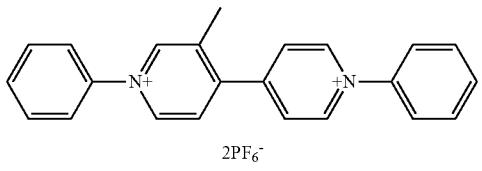
2PF$_6^-$
B-2
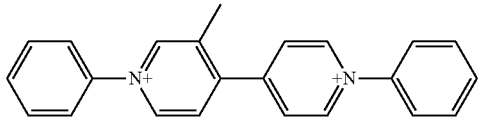
2(CF$_3$SO$_2$)$_2$N$^-$
B-3
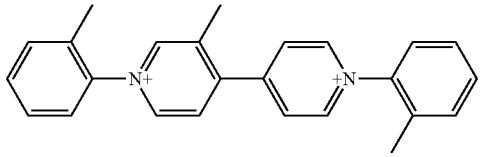
2(CF$_3$SO$_2$)$_2$N$^-$
B-4
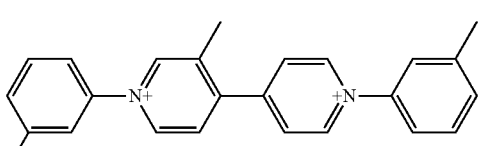
2CF$_3$SO$_3^-$
B-5
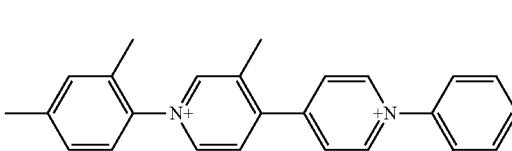
2PF$_6^-$
B-6
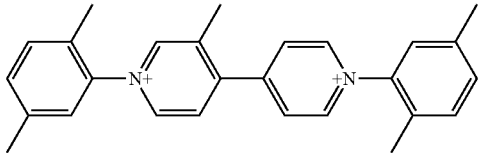
2PF$_6^-$ B-7
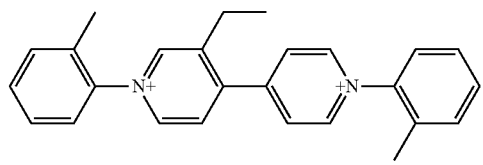
2PF$_6^-$
B-8
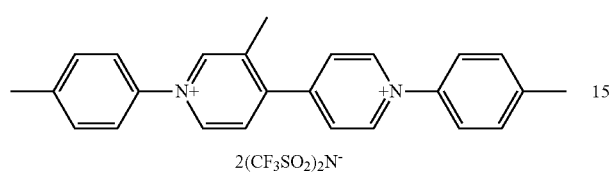
2(CF$_3$SO$_2$)$_2$N$^-$
B-9
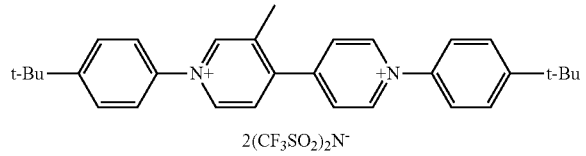
2(CF$_3$SO$_2$)$_2$N$^-$
B-10
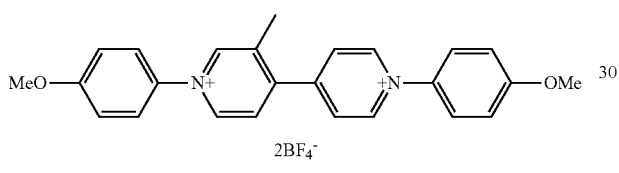
2BF$_4^-$
B-11
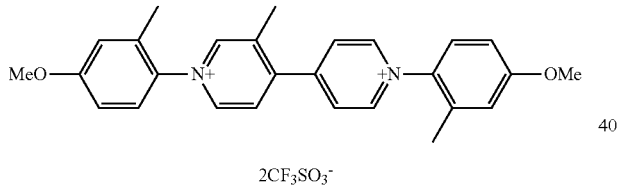
2CF$_3$SO$_3^-$
B-12
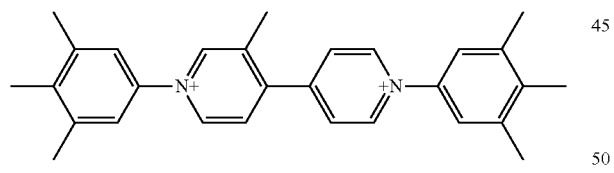
2(CF$_3$SO$_2$)$_2$N$^-$
B-13
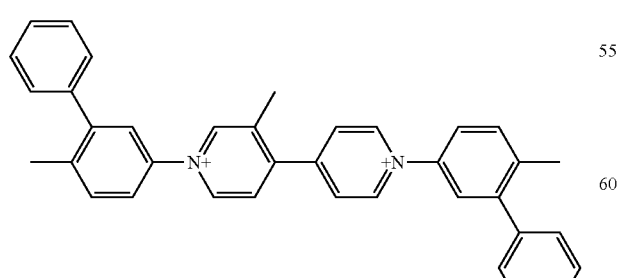
2(CF$_3$SO$_2$)$_2$N$^-$
B-14
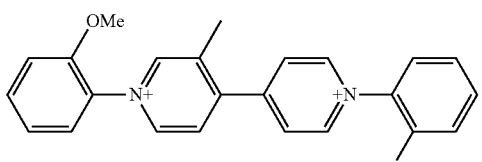
2PF$_6^-$
C-1
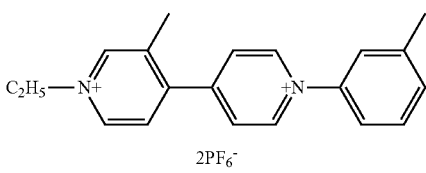
2PF$_6^-$
C-2
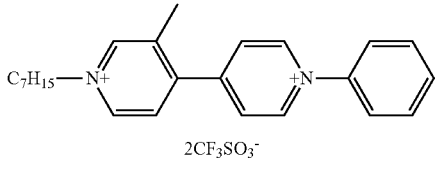
2CF$_3$SO$_3^-$
C-3
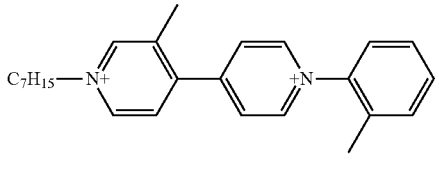
2(CF$_3$SO$_2$)$_2$N$^-$
C-4
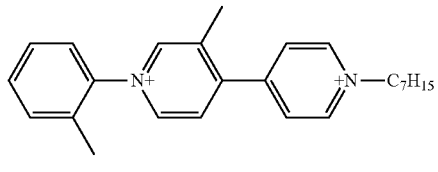
2(CF$_3$SO$_2$)$_2$N$^-$
C-5
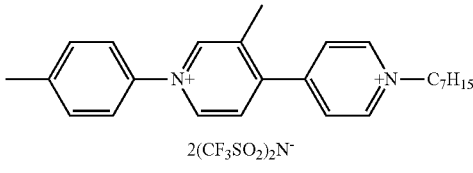
2(CF$_3$SO$_2$)$_2$N$^-$
C-6
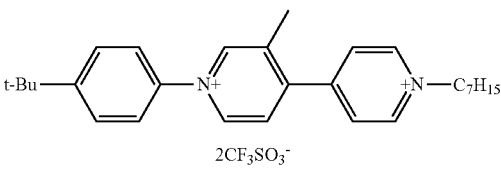
2CF$_3$SO$_3^-$
C-7
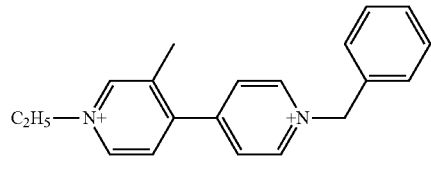
2PF$_6^-$

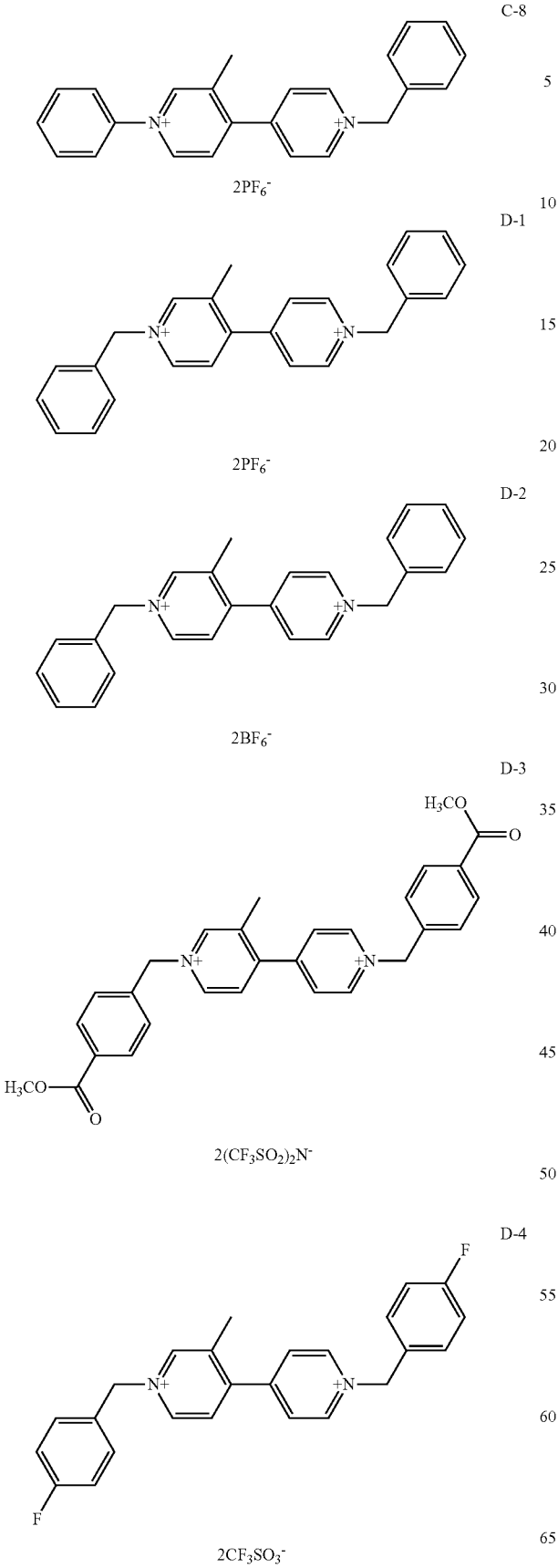
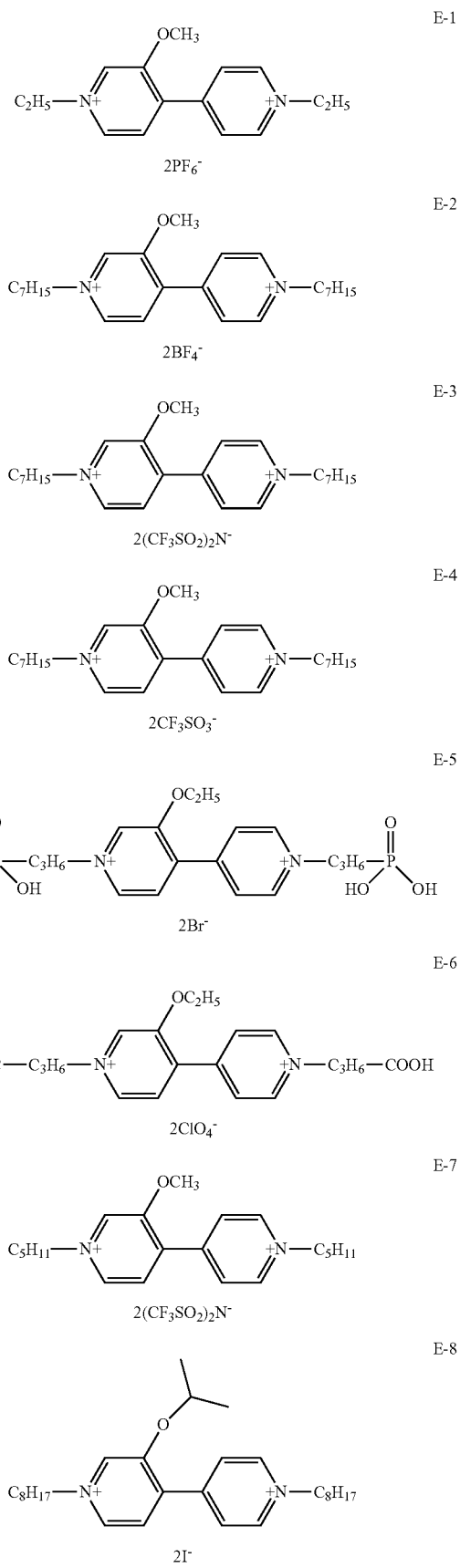

-continued
F-1
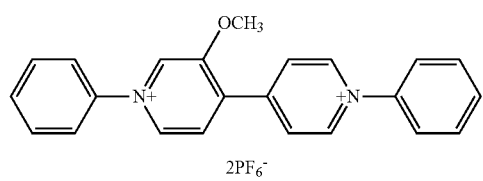
2PF$_6^-$
F-2
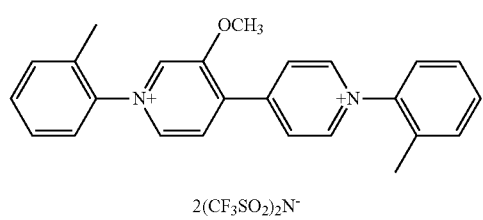
2(CF$_3$SO$_2$)$_2$N$^-$
F-3
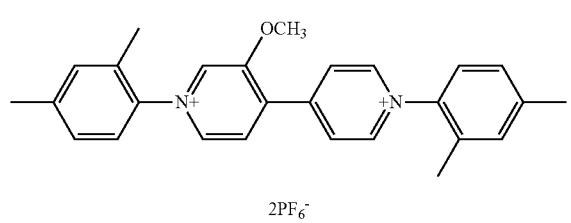
2PF$_6^-$
F-4
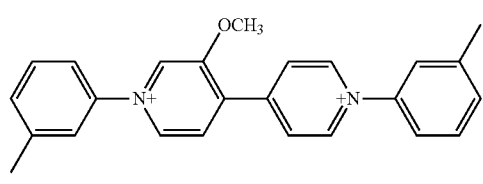
2CF$_3$SO$_3^-$
F-5
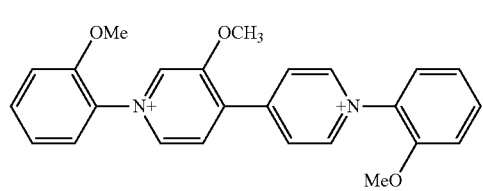
2PF$_6^-$
F-6
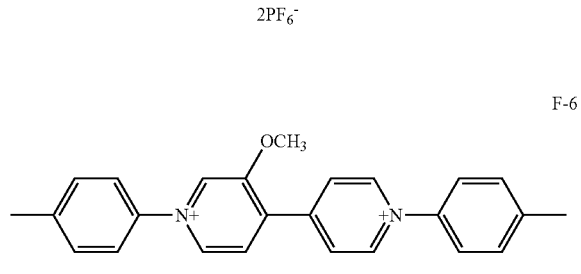
2(CF$_3$SO$_2$)$_2$N$^-$
F-7
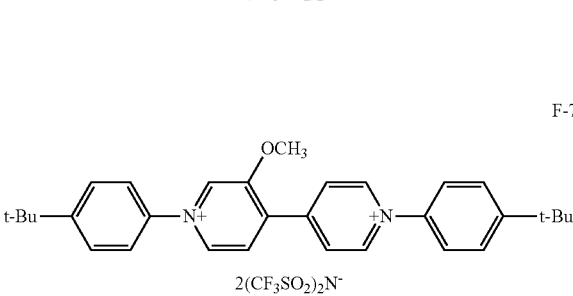
2(CF$_3$SO$_2$)$_2$N$^-$
-continued
F-8
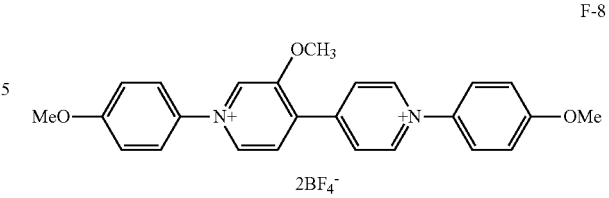
2BF$_4^-$
F-9
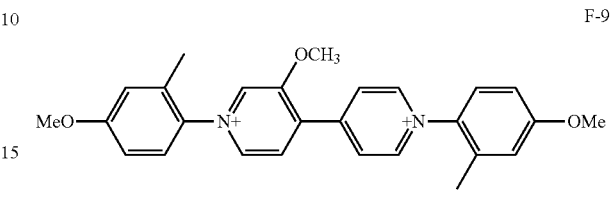
2CF$_3$SO$_3^-$
F-10
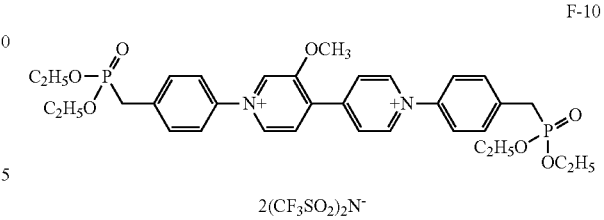
2(CF$_3$SO$_2$)$_2$N$^-$
G-1
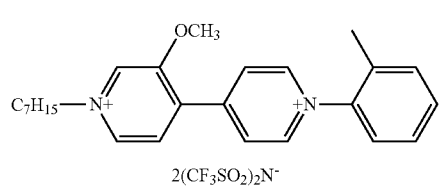
2(CF$_3$SO$_2$)$_2$N$^-$
G-2
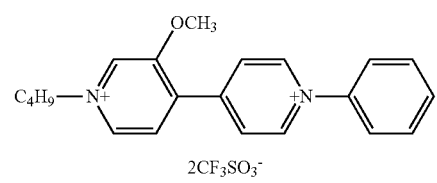
2CF$_3$SO$_3^-$
G-3
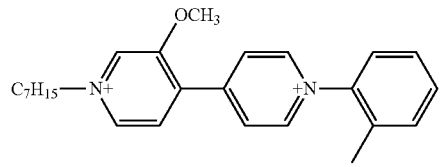
2(CF$_3$SO$_2$)$_2$N$^-$
G-4
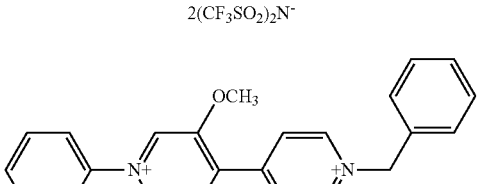
2PF$_6^-$
G-5
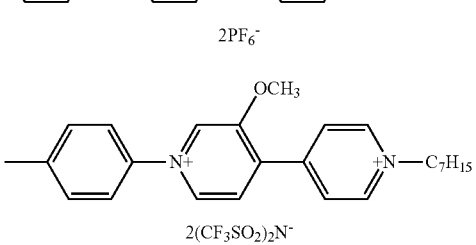
2(CF$_3$SO$_2$)$_2$N$^-$ -continued

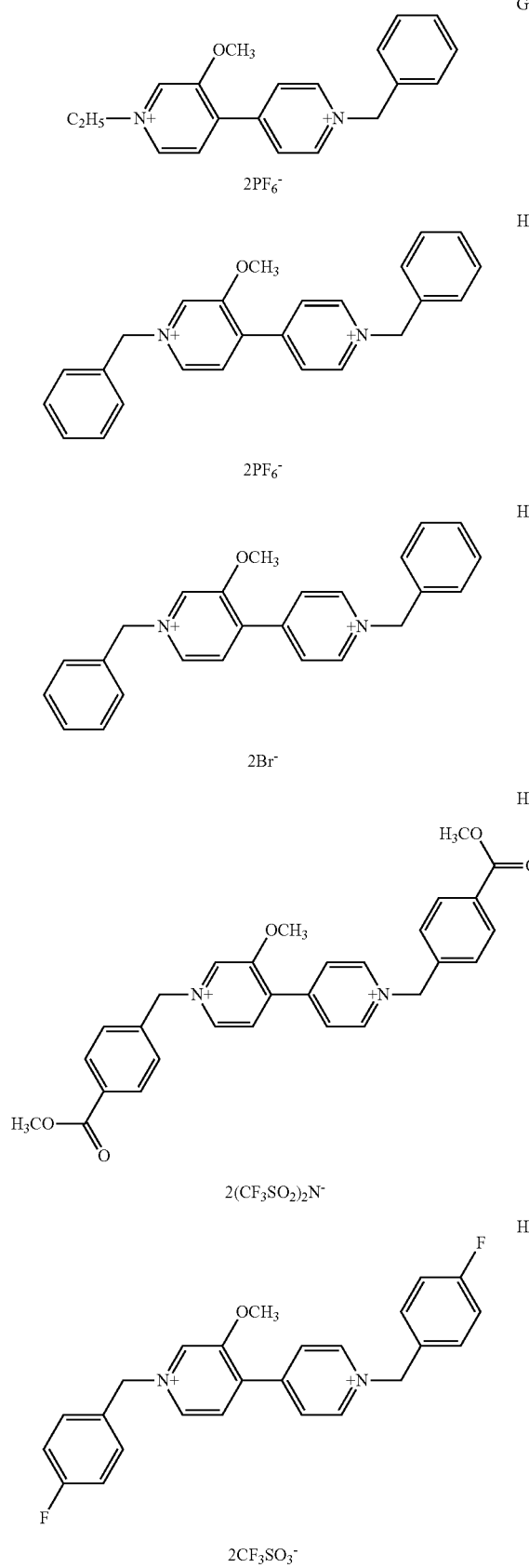

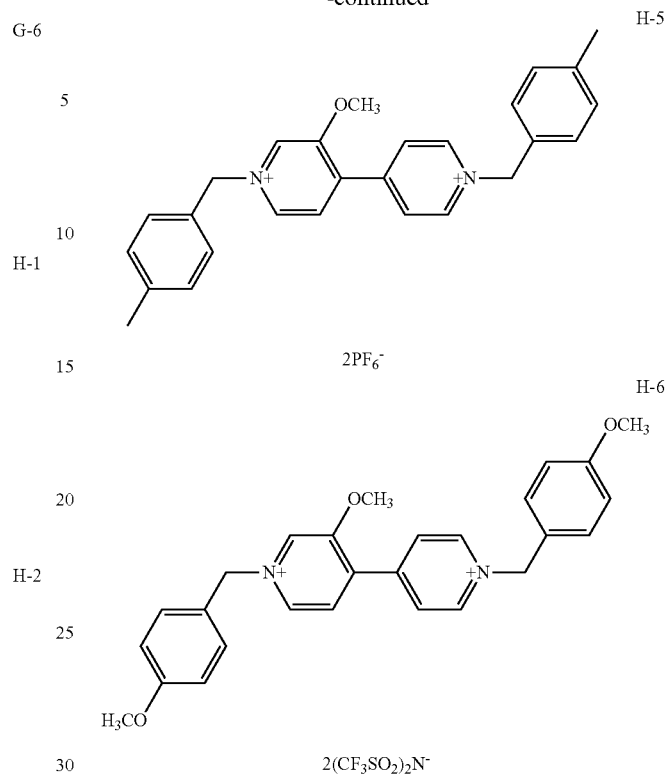

As described above, according to the organic compound represented by General Formula (1) of this embodiment, an organic compound having the absorption peak in a long wavelength band as compared with that of viologen in which no substituents are introduced into the carbon atoms of 4,4'-bipyridinium in a colored state and in which a redox reaction reversibly progresses can be provided.

Second Embodiment

The organic compound of the first embodiment has the EC property and is usable for an electrochromic layer (EC layer) of an EC element. Hereinafter, an EC element according to this embodiment is described with reference to FIG. 1.

FIG. 1 is a frame format illustrating an example of the configuration of an EC element 15 of this embodiment. The EC element 15 is an EC element having a pair of electrodes 11, an EC layer 12 disposed between the pair of electrodes 11, a pair of substrates 10, and a spacer 13. The pair of electrodes 11 is configured so that the distance between the electrodes is fixed by the spacer 13. In the EC element 15 of this embodiment, the pair of electrodes 11 is disposed between the pair of substrates 10. The EC element 15 of this embodiment has the pair of electrodes 11, the EC layer 12, the pair of substrates 10, and the spacer 13 but the EC element may have at least the pair of electrodes 11 and the EC layer 12 and may not have the substrates 10 and the spacer 13.

The EC layer 12 has an electrolyte and the electrochromic organic compound of this embodiment. The EC-layer 12 may have a layer containing an EC compound and a layer containing an electrolyte. Moreover, the EC layer 12 may be provided as a solution having an EC compound and an electrolyte. The EC element 15 according to this embodiment is suitably an EC element in which the EC layer 12 is a solution.

Next, members forming the EC element 15 according to this embodiment are described.

The electrolyte is not limited insofar as it is an ion dissociative salt and snows good solubility in a solvent and, in a solid electrolyte, shows high compatibility. In particular, an electrolyte having electron donation properties is suitable. These electrolytes can also be referred to as supporting electrolytes.

Examples of the electrolyte include, for example, inorganic ion salts, quaternary ammonium salts, cyclic quaternary ammonium salts, such as various kinds of alkaline metal salts and alkaline earth metal salts, and the like.

Specifically, alkaline metal salts of Li, Na, and K, such as $LiClO_4$, $LiSCN$, $LiBF_4$, $LiAsF_6$, $LiCF_3SO_3$, $LiPF_6$, LiI, NaI, NaSCN, $NaClO_4$, $NaBF_4$, $NaAsF_6$, KSCN, and KCl, quaternary ammonium salts and cyclic quaternary ammonium salts, such as $(CH_3)_4NBF_4$, $(C_2H_5)_4NBF_4$, $(n-C_4H_9)_4NBF_4$, $(n-C_4H_9)_4NPF_6$, $(C_2H_5)_4NBr$, $(C_2H_5)_4NClO_4$, and $(n-C_4H_9)_4 NClO_4$, and the like are mentioned.

The solvent dissolving the EC organic compound and the electrolyte is not particularly limited insofar as the EC organic compound and the electrolyte can be dissolved, and particularly those having polarity are suitable.

Specifically, water and organic polar solvents, such as methanol, ethanol, propylene carbonate, ethylene carbonate, dimethylsulfoxide, dimethoxyethane, γ-butyrolactone, γ-valerolactone, sulfolane, dimethyl formamide, tetrahydrofuran, acetonitrile, propionenitrile, benzonitrile, dimethyl acetamide, methylpyrrolidone, and dioxolane are mentioned.

Furthermore, those obtained by further compounding a polymer or a gelling agent in the above-described EC media mentioned above so as to high viscosity or having a gel shape are also usable.

The above-described polymer is not particularly limited and, for example, polyacrylonitrile, carboxymethylcellulose, polyvinyl chloride, polyethylene oxide, polypropylene oxide, polyurethane, polyacrylate, polymethacrylate, polyamide, polyacrylamide, polyester, Nafion (Registered Trademark), and the like are mentioned.

Next, the substrates 10 and the electrodes 11 are described. The substrates 10 are suitably transparent substrates. In this embodiment, the "transparent" refers to the fact that the transmittance of visible light is a transmittance of 90% or more.

As materials of the substrates 10, colorless or colored glass, tempered glass, and the like are used, and, in addition thereto, colorless or colored transparent resin is used, for example. Specifically, polyethyleneterephthalate, polyethylenenaphthalate, polynorbornene, polyamide, polysulfone, polyether sulfone, polyetheretherketone, polyphenylene sulfide, polycarbonate, polyimide, polymethylmethacrylate, and the like are mentioned.

The electrodes 11 are suitably transparent electrodes. In this embodiment, both the pair of electrodes 11 are transparent electrodes but the present disclosure is not limited thereto and materials may be selected as appropriate according to the intended use, e.g., one of the pair of electrodes 11 is a transparent electrode.

As materials of the electrodes 11, for example, metals and metal oxides, such as indium tin oxide alloy (ITO), fluoride doped tin oxide (FTO), tin oxide (NESA), indium, zinc oxide (IZO (Registered Trademark)), silver oxide, vanadium oxide, molybdenum oxide, gold, silver, platinum, copper, indium, and chromium, silicon-based materials, such as polycrystalline silicon and amorphous silicon, carbon materials, such as carbon black, graphite, and glassy carbon, and the like can be mentioned. Moreover, complexes of a conductive polymer having conductivity increased by doping treatment or the like, e.g., polyaniline, polypyrrole, polythiophene, polyacetylene, polyparaphenylene, and polyethylene dioxy thiophene (PEDOT), and polystyrene sulfonate and the like are suitably used.

Furthermore, a porous electrode may be provided on the electrode. For the porous electrode, materials having a large surface area of a porous shape, a rod shape, a wire shape, and the like in which fine pores are formed in the surface or inside thereof are suitable. As materials of the porous electrode, metals, metal oxides, carbon, and the like are applicable, for example. More suitably, metal oxides, such as titanium oxide, tin oxide, iron oxide, strontium oxide, tungsten oxide, zinc oxide, tantalum oxide, vanadium oxide, indium oxide, nickel oxide, manganese oxide, and cobalt oxide, are mentioned.

The spacer 13 is disposed between the pair of electrodes 11 and gives space for accommodating the solution (EC layer 12) having the EC organic compound of this embodiment. As materials of the spacer 13, polyimide, polytetrafluoroethylene, fluororubber, epoxy resin, and the like are specifically usable. By the spacer, the distance between the electrodes 11 can be held.

The EC element 15 according to this embodiment may have an injection port (not illustrated) for injecting a composition having the EC organic compound into the space formed by the pair of electrodes 11 and the spacer 13. The composition having the EC organic compound is charged from the injection port, the injection port is covered with a sealing member, and then the injection port is tightly sealed with an adhesive or the like, whereby an element can be formed. The sealing member also has a function of separating the adhesive and the organic compound having the EC property so as not to contact each other. The shape of the sealing member is not particularly limited and is suitably a tapered shape, such as a wedge shape.

A method for forming the EC element 15 according to this embodiment is not particularly limited. For example, as the method for forming the EC element 15, a method can be used which includes injecting liquid containing the EC organic compound prepared beforehand into the space provided between electrode substrates as the pair of electrodes 11 by a vacuum, injection method, an air injection method, a meniscus method, or the like to form the EC layer 12.

The EC element 15 may have the organic compound of this embodiment and a second organic compound different in type from the organic compound. As the second organic compound, one type or a plurality of types may be acceptable and a compound which is colored in an oxidized state, a compound which is colored in a reduced state, or a compound having both the properties may be acceptable. Since the organic compound, according to this embodiment is a compound which is colored in a reduced state, the second organic compound is suitably a compound which is colored in an oxidized state.

The compound which is colored in an oxidized state is a compound in which the transmittance of visible light in an oxidized state is lower than the transmittance of visible light in a reduced state.

The organic compound of this embodiment can develop a desired color as the EC element by being combined with coloring materials of other colors. The organic compound of the different type in coloring suitably has an absorption wavelength in the range of 400 nm or more and 800 nm or less and more suitably has an absorption wavelength in the range of 420 nm or more and 700 nm or less.

The description of "having an absorption wavelength in a specific range" refers to the fact that at least one absorption peak, of the absorption spectrum may fall within a specific wavelength range.

By combining the material of this embodiment and a plurality of other materials, an EC element which absorbs all visible regions and is colored black can also be produced.

As the second organic compound according to this embodiment, the following compounds are mentioned, for example.

Examples of other EC compounds which are colored in an oxidized state include phenazine compounds, such as 5,10-dihydro-5,10-dimethylphenazine and 5,10-dihydro-5,10-diethylphenazine, metallocene compounds, such as ferrocene, tetra-t-butylferrocene, and titanocene, phenylenediamine compounds, such as N,N',N,N'-tetramethyl-p-phenylenediamine, pyrazoline compounds, such as 1-phenyl-2-pyrazoline, and the like.

Examples of the compound which is colored in a reduced state include viologen compounds, such as N,N'-diheptylbipyridinium diperchlorate, N,N'-diheptylbipyridinium ditetrafluoroborate, N,N'-diheptylbipyridinium dihexafluorophosphate, N,N'-diethylbipyridinium diperchlorate, N,N'-diethylbipyridinium ditetrafluoroborate, N,N'-diethylbipyridinium dihexafluorophosphate, N,N'-dibenzylbipyridinium diperchlorate, N,N'-dibenzylbipyridinium ditetrafluoroborate, N,N'-dibenzylbipyridinium dihexafluorophosphate, N,N'-diphenylbipyridinium diperchlorate, N,N'-diphenylbipyridinium ditetrafluoroborate, and N,N'-diphenylbipyridinium dihexafluorophosphate, anthraquinone compounds, such as 2-ethylanthraquinone, 2-t-butylanthraquinone, and octamethylanthraquinone, ferrocenium salt compounds, such as ferrocenium tetrafluoroborate and ferrocenium hexafluorophosphate, a styryl compound, and the like.

Among the above, the second organic compound is suitably any one of the phenazine compounds, the ferrocene compounds, the metallocene compounds, the phenylenediamine compounds, and the pyrazoline compounds. Moreover, the organic compound of the different type represented by General Formula (1) above may be included as the second organic compound. More specifically, the EC element may have two or more of the organic compounds which each are represented by General Formula (1) and different from each other.

The compound contained in the EC layer 12 of the EC element 15 according to this embodiment can be confirmed to be contained in the EC element 15 by extracting and analyzing the compound by a known method. For example, the compound is extracted by chromatography and analyzed by NMR. When the electrochromic layer is a solid, the analysis can be performed by TOF-SIMS or the like.

Third Embodiment

The EC element of the second embodiment is usable for an optical filter, a lens unit, an imaging device, and the like. This embodiment describes an optical filter, a lens unit, and an imaging device employing an EC element-containing the organic compound represented by General Formula (1) in an EC layer.

The optical filter according to this embodiment has an EC element 15 of this embodiment and an active element connected to the EC element 15. The active element drives the EC element 15, and adjusts the amount of light passing through the EC element 15. Examples of the active element include a transistor, an MIM element, and the like, for example. The transistor may have an oxide semiconductor, such as InGaZnO, in an active region.

It is desired that, when the EC element 15 is used for an optical filter, a lens unit, and an imaging device, the color in a colored state of the EC element does not change particularly with temperatures. When coloring changes, the color of the optical filter shifts, which causes color change in a target image. Although it is also considered that the coloring amount changes with temperature changes, this problem can be overcome by changing a drive voltage and drive time.

The lens unit employing the EC element 15 has the above-described optical filter and an imaging optical system. The imaging optical system is a lens group having a plurality of lenses. The optical filter of the lens unit may be disposed between the lenses or, when attached, to an imaging device, may be provided so as to be disposed on the side of the imaging element relative to the lenses. When attached, to an imaging device, the optical filter may be provided so as to be disposed on the outside relative to the lenses.

The imaging device employing the EC element 15 has the imaging optical system, the above-described optical filter, and an imaging element receiving light passing through the optical filter. The imaging device according to this embodiment is a digital camera or a digital video camera, for example. The optical filter of the imaging device according to this embodiment may be provided immediately before the imaging element. The "immediately before the imaging element" means that there is no member disposed between the imaging device and the optical filter. When the imaging device has a lens, the optical filter may be provided outside the lens. The "optical filter is provided outside the lens" refers to the fact that the optical filter is disposed so that the lens is disposed between the optical filter and the imaging element. When the imaging device has a plurality of lenses, the optical filter may be provided between the lenses.

Figure 2A:
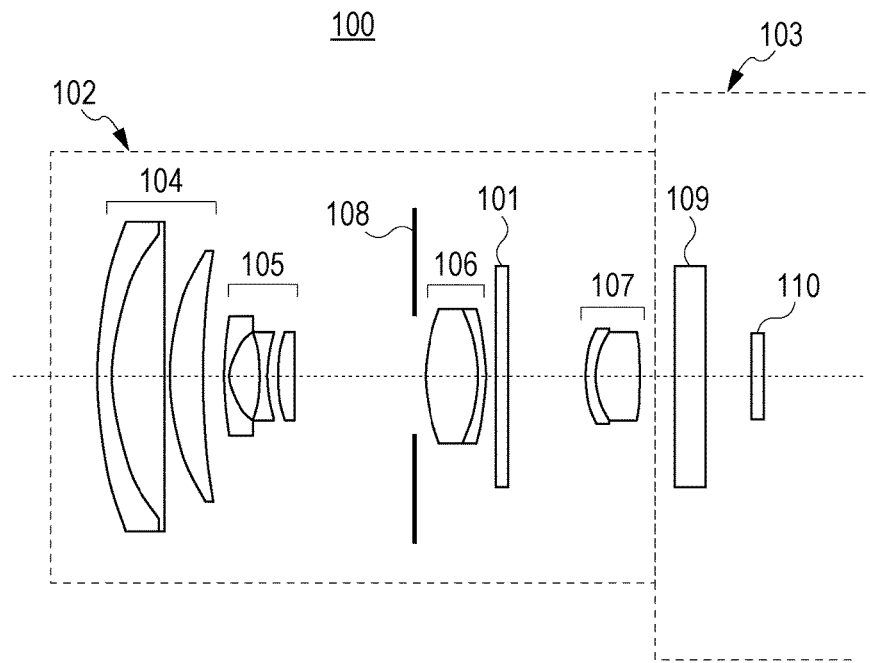
FIGS. 2A and 2B are cross-sectional frame formats explaining the configuration of an imaging device according to an embodiment of the subject application.

FIG. 2A is a frame format illustrating an imaging device 100 of this embodiment. The imaging device 100 of this embodiment has a lens unit 102 and an imaging unit 103, in which the lens unit 102 is detachably connected to the imaging unit 103 through a mount member (not illustrated). The imaging unit 103 has a glass block 109 and an imaging element 110.

The lens unit 102 is a unit having an imaging optical system containing a plurality of lenses or a lens group and is a zoom lens of a rear focus type which performs focusing on the side of the imaging element 110 relative to a stop.

The lens unit 102 has an imaging optical system, an aperture stop 108, and an optical filter 101. The imaging optical system of the lens unit 102 contains four lens groups of a first lens group 104 of positive refractive power, a second lens group 105 of negative refractive power, a third lens group 106 of positive refractive power, and a fourth lens group 107 of positive refractive power in order from the side of an object. The aperture stop 108 is disposed between the second lens group 105 and the third lens group 106. The optical filter 101 is disposed between the third lens group 106 and the fourth lens group 107.

By changing the interval between the second lens group 105 and the third lens group 106 to perform zooming, some lens groups of the fourth lens group 107 are moved to perform focusing. Each member is disposed so that light passing through the first to fourth lens groups 104 to 107, the aperture stop 108, and the optical filter 101 is received by the imaging element 110. The amount of light received by the imaging element 110 can be adjusted using the aperture stop 108 and the optical filter 101. The optical filter 101 has the EC element 15 of this embodiment.

The glass block 109 is a glass block, such as a low pass filter, a faceplate, and a colored filter.

The imaging element 110 is a sensing section receiving light passing through the lens unit 102, and imaging elements, such as a CCD and a CMOS sensor, are usable therefor. An optical sensor, such as a photodiode, may be acceptable and those capable of acquiring and outputting information on the intensity or the wavelength of light are usable as appropriate.

In the imaging device of this embodiment, the optical filter 101 employing the EC element 15 is disposed between the third lens group 106 and the fourth lens group 107 in the lens unit 102 as an example. In the imaging device of this embodiment, the position of the optical filter 101 is not limited to the arrangement and the optical filter 101 may be disposed either in front of or behind the aperture stop 108 or may be disposed in front of or behind the first to fourth lens groups 104 to 107 or between the first to fourth lens groups 104 to 107.

By disposing the same at a position where light-converges, advantages that the area of the optical filter can be made small and the like are obtained. In the imaging device of the present disclosure, the type of the lens unit can be selected as appropriate and an inner focus type which performs focusing before the stop may be acceptable besides the rear focus type, and other types may be acceptable. Besides the zoom lens, special lenses, such as a fish-eye lens and a macrolens, are also selectable as appropriate.

In the imaging device of this embodiment, the optical filter 101 is disposed inside the lens unit 102 as an example. In the imaging device of this embodiment, the EC element 15 of the optical filter 101 is present in the lens unit 102 and a drive device of the EC element 15 may be disposed outside the lens unit 102, i.e., in the imaging unit 103. In such a case, the EC element 15 in the lens unit 102 and the drive device of the EC element 15 are connected through wiring, and drive control is performed.

Figure 2B:
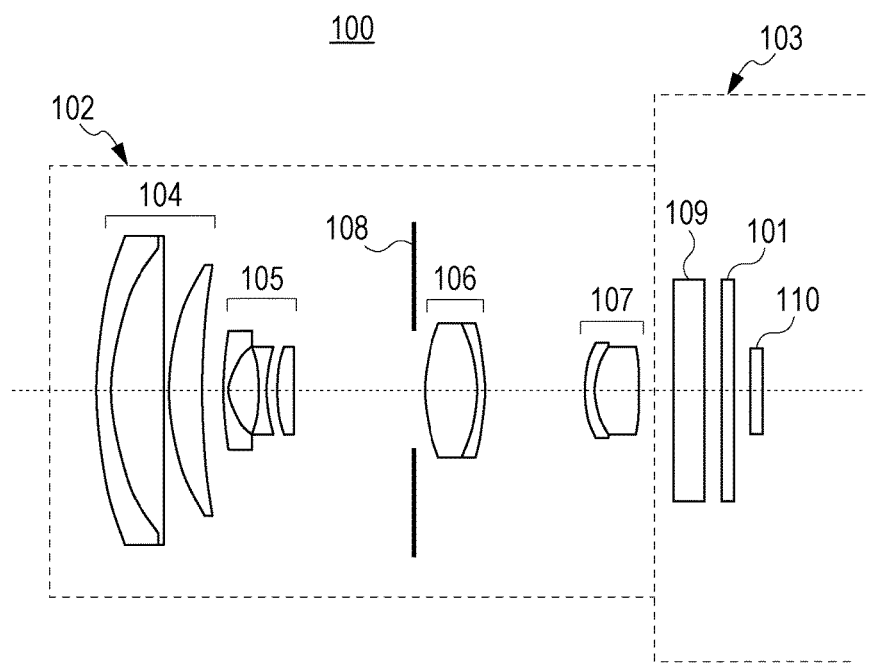

FIG. 2B illustrates a frame format of another example of the configuration of the imaging device of this embodiment. In the imaging device illustrated in FIG. 2B, the optical filter 101 is disposed inside the imaging unit 103. Thus, the optical filter 101 may be disposed inside the imaging unit 103.

The optical filter 101 is disposed between the glass block 109 and the imaging element 110 inside the imaging unit 103. When the imaging unit 103 itself contains the optical filter 101 therein, an existing lens unit is usable because the lens unit 102 to be connected does not need to have an optical filter.

FIG. 2A and FIG. 2B are examples of the configuration of the imaging device 100. The imaging element 110 may be disposed so as to receive light passing through the optical filter 101. The optical filter 101 may be disposed at positions other than the position between the imaging element 110 and the glass block 109.

Examples of such an imaging device 100 include a product and the like having a combination of light amount adjustment and an imaging element, for example, and the imaging device 100 may be an imaging portion of a camera, a digital camera, a video camera, a digital video camera, a cellular phone and a smart phone, a PC, a tablet, and the like.

Fourth Embodiment

The EC element of the second embodiment is usable for a window component. This embodiment describes a window component employing an EC element containing the organic compound represented by General Formula (1) in an EC layer.

The window component employing the EC element 15 has the EC element 15 and an active element connected to the EC element 15. The amount of light passing through a pair of substrates 10 can be adjusted by the EC element 15. When the window component is combined with a window frame and the like, a window is obtained. The window component is usable for a window of an automobile, a window of an airplane, a window of a building material, and the like. In the window component employing the EC element, the EC element does not necessarily need to have the substrates 10 and the spacer 13 and may have the pair of electrodes 11 and an EC layer 12.

EXAMPLES

Hereinafter, Examples are described but the present disclosure is not limited to Examples described below.

Example 1

Synthesis of Exemplary Compound A-2

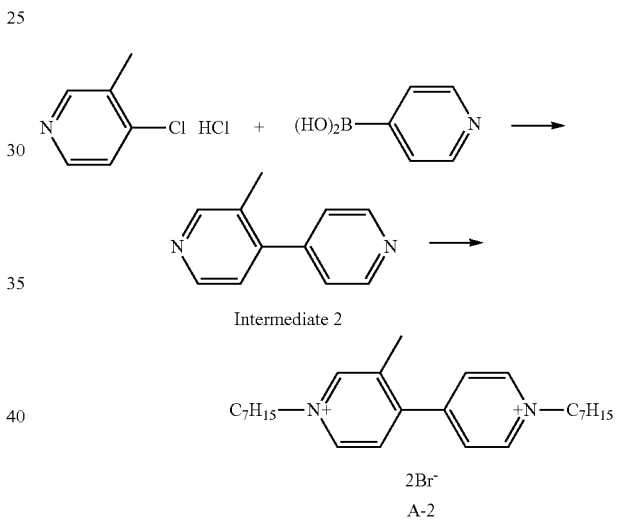

For the synthesis of Exemplary Compound A-2, an intermediate 2 was first synthesized. In a reaction container, 3-methyl-4-chloropyridine hydrochloride (0.58 g, 3.6 mmol), 4-pyridyl boronic acid (0.65 g, 5.3 mmol), tris (dibenzylideneacetone)dipalladium (0) (65 mg, 0.07 mmol), tricyclohexylphosphine (45 mg, 0.16 mmol), tripotassium-phosphate (n hydrate) (2 g), dioxane (10 ml), and water (6 ml) were charged, and then, stirred under heating and refluxing under a nitrogen stream for 8 hours. After the completion of a reaction, the reaction liquid was condensed, and then, extracted with ethyl acetate. An organic layer was washed with water, dried over magnesium sulfate, and then dried under reduced pressure. The resultant substance was purified, by silica gel chromatography (Eluate: chloroform/methanol=30/1), and then recrystallized with diisopropyl-ether/hexane to give 0.54 g (Yield: 90%) of intermediate 2.

The structure of the intermediate 2 was confirmed by NMR measurement.

$^1$H NMR (CDCl$_3$, 500 MHz) σ (ppm): 8.72 (m, 2H), 8.56 (s, 1H), 8.53 (d, 1H), 7.26 (m, 2H), 7.14 (d, 1H), 2.29 (s, 3H)

Next, Exemplary Compound A-2 was synthesized from the intermediate 2. The intermediate 2 (170 mg, 1 mmol), 1-bromoheptane (537 mg, 3 mmol), and 10 ml of N,N-dimethylformamide were charged in a reaction container, and then stirred at 100° C. under a nitrogen stream for 8 hours. After the completion of a reaction, ethyl acetate was added dropwise to the reaction liquid, and then the obtained crystal was washed with ethyl acetate to give 375 mg (Yield: 71%) of Exemplary Compound A-2.

The structure of Exemplary Compound A-2 was confirmed by NMR measurement.

$^1$H NMR (DMSO-d6, 500 MHz) σ (ppm): 9.31 (d, 2H), 9.27 (s, 1H), 9.16 (d, 1H), 8.37 (d, 2H), 8.19 (d, 1H), 4.68 (t, 2H), 4.64 (t, 2H), 2.44 (s, 3H), 1.97 (m, 4H), 1.40-1.20 (m, 16H), 0.86 (t, 6H)

Example 2

Synthesis of Exemplary Compound A-6

Exemplary Compound A-6 was synthesized from Exemplary Compound A-2. First, Exemplary Compound A-2 (106 mg, 0.2 mmol) was dissolved in water. An aqueous solution in which potassium hexafluorophosphate (200 mg) was dissolved was added dropwise, and then stirred at room temperature for 3 hours. The deposited crystal was filtered, and then successively washed with, isopropyl alcohol and diethylether to give 129 mg (Yield: 98%) of Exemplary Compound A-6.

The structure of Exemplary Compound A-6 was confirmed by NMR measurement.

$^1$H NMR (CD$_3$CN, 500 MHz) σ (ppm): 8.86 (d, 2H), 8.75 (s, 1H), 8.69 (d, 1H), 8.07 (d, 2H), 7.90 (d, 1H), 4.61 (t, 2H), 4.56 (t, 2H), 2.41 (s, 3H), 2.02 (m, 4H), 1.46-1.26 (m, 16H), 0.91 (t, 6H)

Example 3

Synthesis of Exemplary Compound B-3

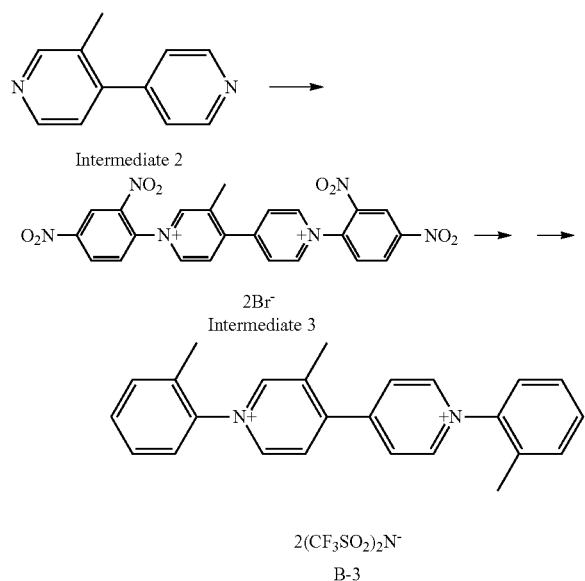

For the synthesis of Exemplary Compound B-3, an intermediate 3 was first synthesized. The intermediate 2 (1.7 g, 10 mmol), 2,4-dinitrobromobenzene (7.4 g, 30 mmol), and N,N-dimethylformamide (100 ml) were charged in a reaction container, and then stirred at 100° C. for 24 hours. After the completion of a reaction, the deposited crystal was filtered, and then washed with acetonitrile to give 4.7 mg (Yield: 70%) of intermediate 3.

The intermediate 3 (332 mg, 0.5 mmol), o-toluidine (536 mg, 5 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, and then an aqueous solution in which bis(trifluoromethanesulfonyl)imidelithium (1 g) was dissolved was added dropwise. Then, the resultant substance was stirred at room temperature for 3 hours, and then isopropyl alcohol was further added for recrystallization to give 374 mg (Yield: 82%) of Exemplary Compound B-3.

The structure of Exemplary Compound B-3 was confirmed by NMR measurement.

$^1$H NMR (CD$_3$CN, 500 MHz) σ (ppm): 9.00 (d, 2H), 8.89 (s, 1H), 8.83 (d, 1H), 8.33 (d, 2H), 8.12 (d, 1H), 7.76-7.66 (m, 2H), 7.64-7.51 (m, 6H), 2.57 (s, 3H), 2.27 (s, 3H), 2.25 (s, 3H)

Example 4

Synthesis of Exemplary Compound B-8

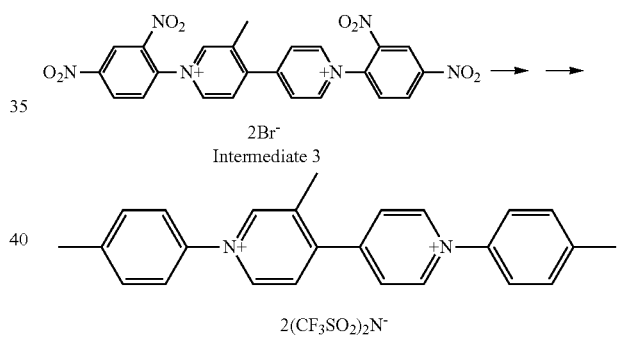

Exemplary Compound B-8 was synthesized from the intermediate 3. The intermediate 3 (332 mg, 0.5 mmol), p-toluidine (161 mg, 1.5 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which bis(trifluoromethanesulfonyl)imidelithium (1 g) was dissolved was added dropwise, the resultant substance was stirred at room temperature for 3 hours, and then the deposited crystal was filtered. The obtained crystal was recrystallized with isopropyl alcohol to give 408 mg (Yield: 88%) of Exemplary Compound B-8.

The structure of Exemplary Compound B-8 was confirmed by NMR measurement.

$^1$H NMR (CD$_3$CN, 500 MHz) σ (ppm): 9.12 (d, 2H), 9.04 (s, 1H), 8.96 (d, 1H), 8.28 (d, 2H), 8.12 (d, 1H), 7.69-7.64 (m, 4H), 7.62-7.57 (m, 4H), 2.56 (s, 3H), 2.53 (m, 6H)

Example 5

Synthesis of Exemplary Compound D-1

The intermediate 2 (170 mg, 1 mmol) synthesized in the same manner as in Example 1, benzylbromide (376 mg, 2.2 mmol), and acetonitrile (10 ml) were charged in a reaction container, and then heated and refluxed under a nitrogen stream for 8 hours. After the completion of a reaction, the deposited crystal was filtered, and then washed with acetonitrile. Then, the obtained crystal was dissolved in water, and then an aqueous solution in which potassium hexafluorophosphate (1 g) was dissolved was added dropwise. Then, the resultant substance was stirred at room temperature for 3 hours, the deposited crystal was filtered, and then the resultant crystal was washed with isopropyl alcohol to give 494 mg (Yield: 77%) of Exemplary Compound D-1.

The structure of Exemplary Compound D-1 was confirmed by NMR measurement.

$^1$H NMR (CD$_3$CN, 500 MHz) σ (ppm): 8.90 (d, 2H), 8.82 (s, 1H), 8.75 (d, 1H), 8.05 (d, 2H), 7.89 (d, 1H), 7.53-7.49 (m, 10H), 5.81 (s, 2H), 5.75 (s, 2H), 2.34 (s, 3H)

Example 6

Production and Evaluation of Properties of Electrochromic Element

In this example, an EC element employing the organic compound represented by General Formula (1) was produced, and then the properties thereof were evaluated. For the organic compound represented by General Formula (1) employed in the EC element of this example, any one of Exemplary Compound A-6 of Example 2, Exemplary Compound B-3 of Example 3, Exemplary Compound B-8 of Example 4, and Exemplary Compound D-1 of Example 5 was used. Tetrabutylammonium perchlorate as an electrolyte was dissolved in propylene carbonate with a concentration of 0.1 M, and then the organic compound represented by General Formula (1) was dissolved with a concentration of 40.0 mM, whereby an EC medium was obtained.

In the EC element, glass substrates with a transparent conductive film (transparent electrode film) as the electrodes 11 were used as the substrates 10. An insulating layer (SiO$_2$) was formed at four end portions of a pair of glass substrates with a transparent conductive film (ITO). A PET film (Melinex (Registered Trademark) S, manufactured by Teijin Du Pont Films, 125 μm thickness) as a spacer defining the substrate interval was disposed between the pair of glass substrates with a transparent electrode film. Thereafter, the glass substrates and the PET film were bonded to each other with an epoxy adhesive, while leaving an injection port for injecting the EC medium, to be sealed. As described above, an empty cell with an injection port was produced.

Next, the EC medium obtained by the method described above was injected from the above-described injection port by a vacuum injection method, and then the injection port was sealed with an epoxy adhesive to provide an EC element.

The EC elements of this example immediately after the production showed a transmittance of about 80% over the entire visible light region and had high transparency in the EC elements employing any one of Exemplary Compounds A-6, B-3, B-8, and D-1.

When a 3.0 V voltage was applied to the EC elements of this example, the EC elements showed the absorption originating from the reduction species of the organic compounds contained in the EC elements, and all the EC elements were colored green. When a −0.5 V voltage was applied, the EC elements decolored, and reversible coloring and decoloring occurred. More specifically, the EC elements of this example can reversibly change a colored state and a decolored state and has the EC property.

Figure 3:
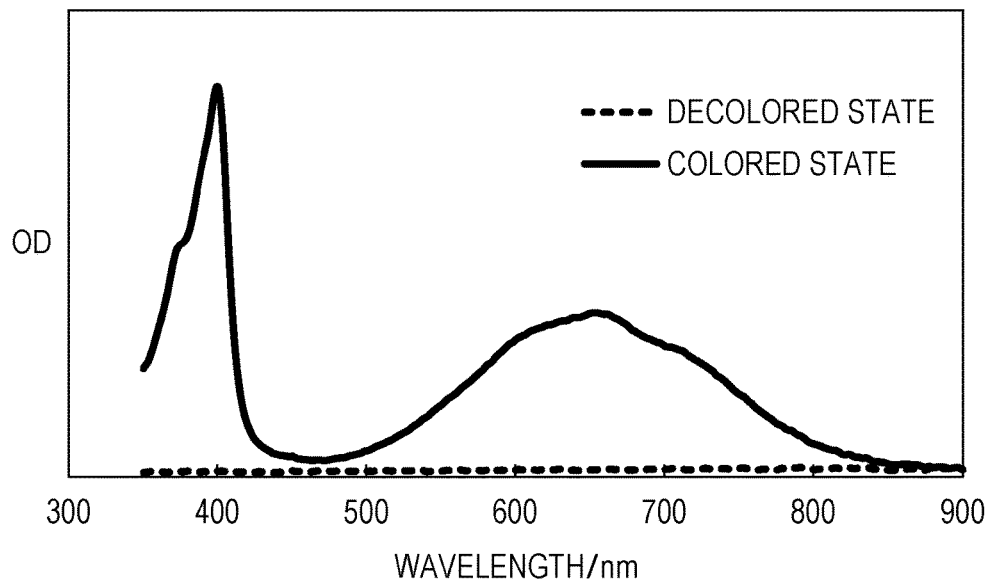
FIG. 3 is the ultraviolet visible absorption spectra in a colored state and a decolored state of Exemplary Compound A-6 according to an embodiment of the subject application.
Figure 4:
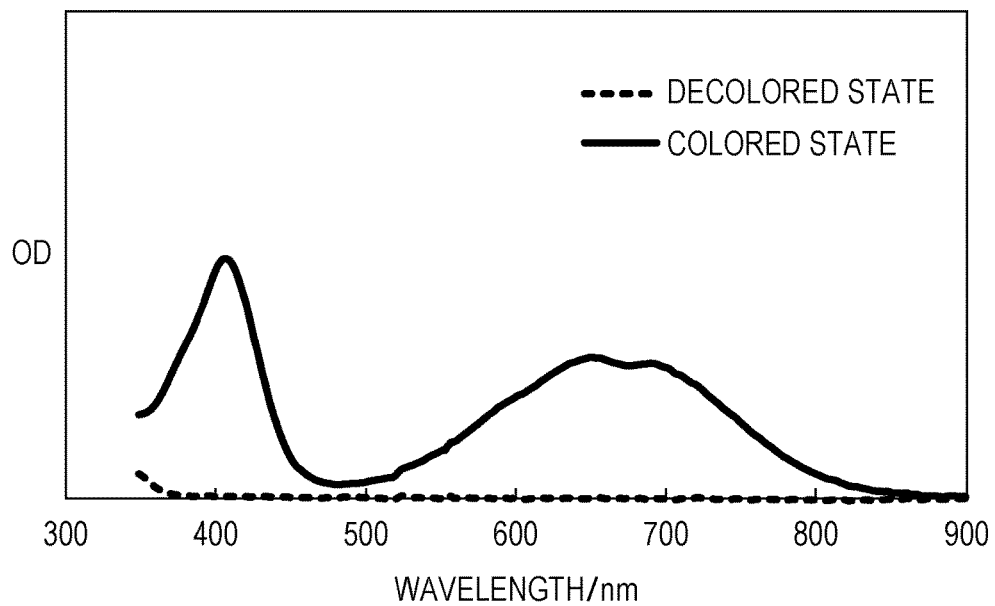
FIG. 4 is the ultraviolet visible absorption spectra in a colored state and a decolored state of Exemplary Compound B-3 according to an embodiment of the subject application.
Figure 5:
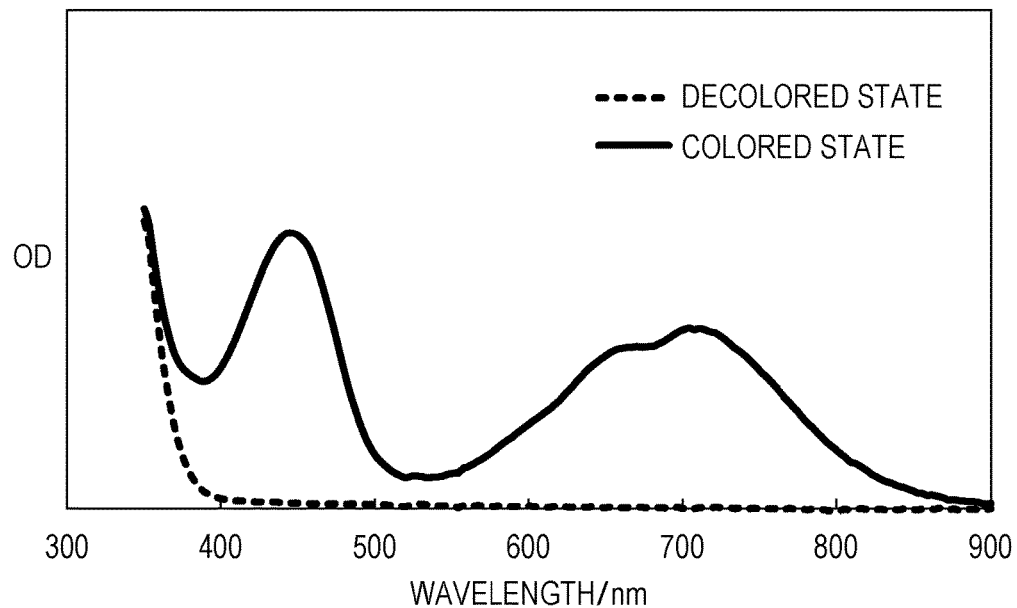
FIG. 5 is the ultraviolet visible absorption spectra in a colored state and a decolored state of Exemplary Compound B-8 according to an embodiment of the subject application.
Figure 6:
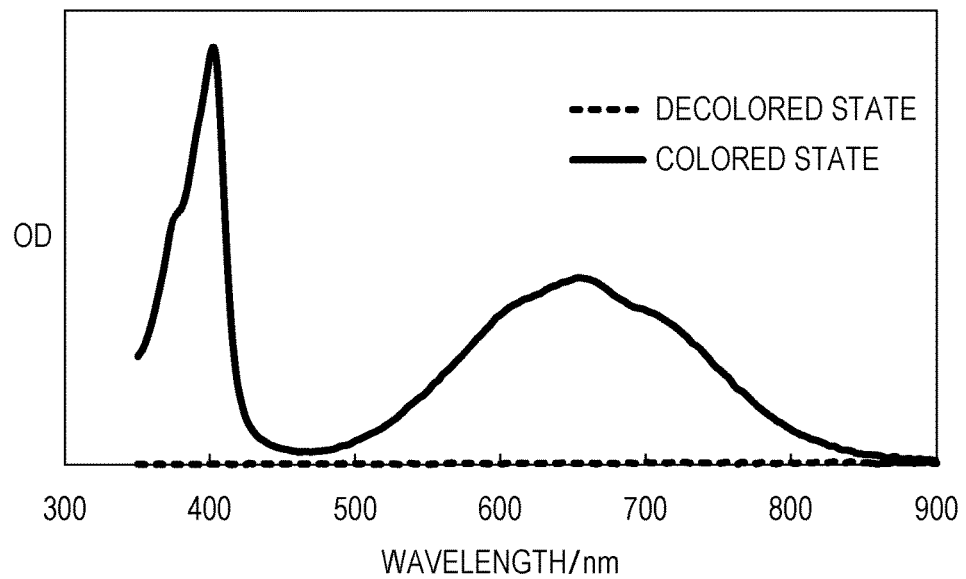
FIG. 6 is the ultraviolet visible absorption spectra in a colored state and a decolored state of Exemplary Compound D-1 according to an embodiment of the subject application.

FIG. 3 to FIG. 6 showed the ultraviolet visible absorption spectra in a colored state and a decolored state of the EC elements of this example. FIG. 3 shows the ultraviolet visible absorption spectra of the EC element-employing Exemplary Compound A-6. FIG. 4 shows the ultraviolet visible absorption spectra of the EC element employing Exemplary Compound B-3. FIG. 5 shows the ultraviolet visible absorption spectra of the EC element employing Exemplary Compound B-8. FIG. 6 shows the ultraviolet visible absorption spectra of the EC element employing Exemplary Compound D-1.

The wavelengths of the absorption peaks of the absorption originating from the reduction species of each of Exemplary Compounds A-6, B-3, B-8, and D-1 in the EC elements of this example are shown below.

Exemplary Compound A-6: 400 nm, 655 nm
Exemplary Compound B-3: 408 nm, 650 nm
Exemplary Compound B-8: 445 nm, 704 nm
Exemplary Compound D-1: 402 nm, 654 nm Thus, the organic compound represented by General Formula (1) has the absorption peak in a wavelength band of 650 nm or more in a reduced state (colored state).

Comparative Example 1

An EC element was produced in the same manner as in Example 6, except using Comparative Compound 1 in place of Exemplary Compounds of Examples 1 to 4. Comparative Compound 1 is an organic compound represented by the following structural formula (3) and is a viologen compound in which no substituents are introduced into the carbon atoms of 4,4'-bipyridinium.

Comparative Compound 1

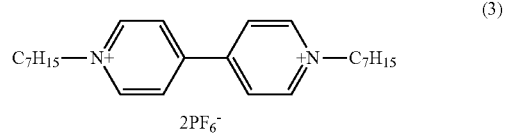

(3)

Figure 7A:
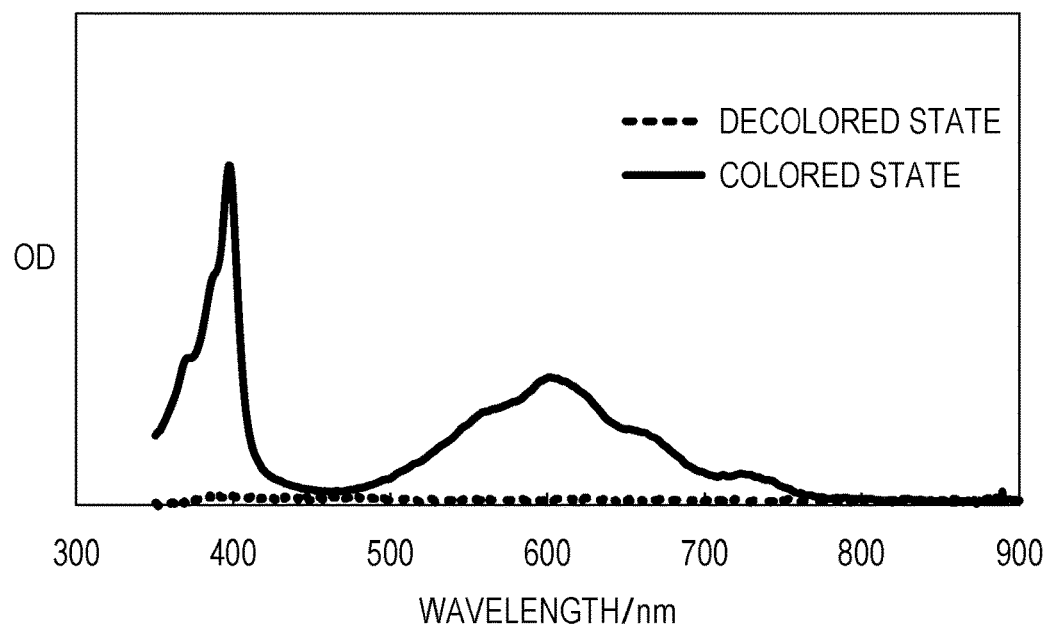
FIGS. 7A and 7B are the ultraviolet visible absorption spectra in a colored state and a decolored state of comparative compounds of Comparative Examples 1 and 2 according to an embodiment of the subject application.

When a 3.0 V voltage was applied to the EC element of this comparative example, the EC element snowed the absorption originating from the reduction species of Comparative Compound 1. FIG. 7A shows the ultraviolet visible absorption spectra of the EC element employing Comparative Compound 1. The wavelengths of the absorption peaks originating from the reduction species of Comparative Compound 1 were 400 nm and 608 nm.

Thus, the organic compound represented by General Formula (1) is an organic compound having the absorption peak in a high wavelength band as compared with that of a viologen compound in which no substituents are introduced into the carbon atoms of 4,4'-bipyridinium in a reduced state (colored state).

Comparative Example 2

An EC element was produced in the same manner as in Example 6, except using Comparative Compound 2 in place of Exemplary Compounds of Examples 1 to 4. Comparative Compound 2 is an organic compound represented by the following structural formula (4) and is a viologen derivative having a methyl group at the second site of 4,4'-bipyridinium.

Comparative Compound 2

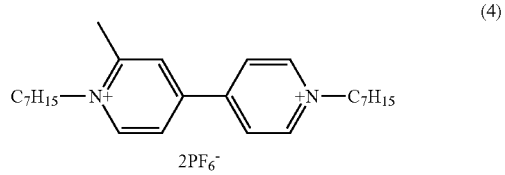

(4)

Figure 7B:
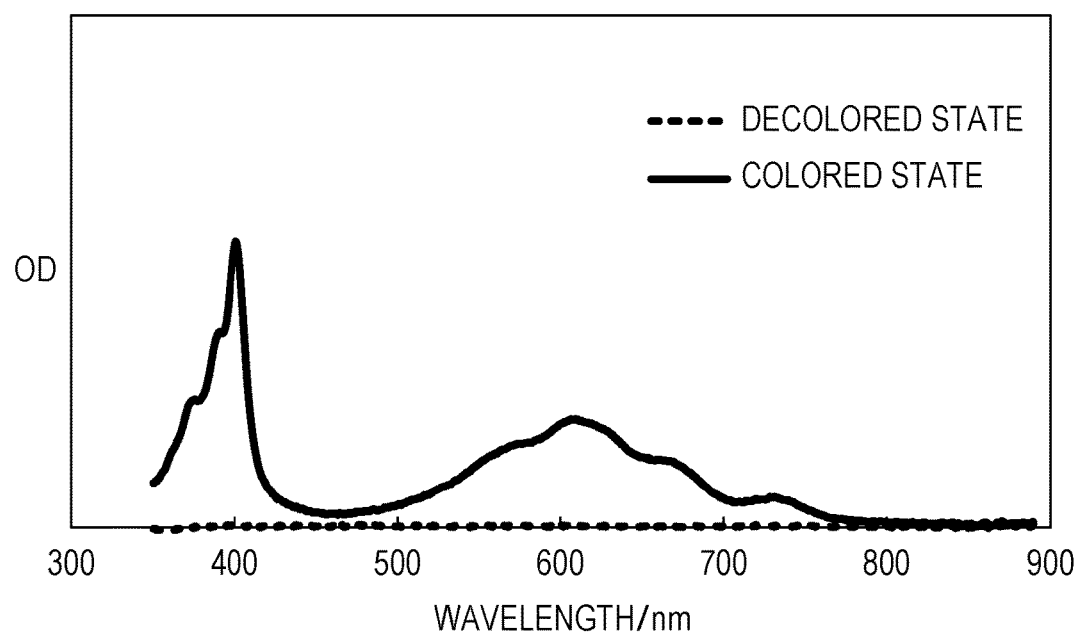

When a 3.0 V voltage was applied to the EC element of this comparative example, the EC element shows the absorption originating from the reduction species of Comparative Compound 2, FIG. 7B shows the ultraviolet visible absorption spectra of the EC element employing Comparative Compound 2. The wavelengths of the absorption peaks of the absorption originating from the reduction species of Comparative Compound 2 were 397 nm and 602 nm.

The wavelength of the absorption peak of the absorption originating from the reduction species of Comparative Compound 2 was almost the same wavelength as the wavelength of the absorption peak in a reduced state of Comparative Compound 1.

Comparative Example 3

An EC element employing Comparative Compound 3 was produced for comparison. The EC element was produced in the same manner as in Example 6, except using Comparative Compound 3 in place of Exemplary Compounds of Examples 1 to 4. Comparative Compound 3 is an organic compound represented by the following structural formula (5) and is a viologen derivative having a methyl group at the 3,3' site of the 4,4'-bipyridinium skeleton.

Comparative Compound 3

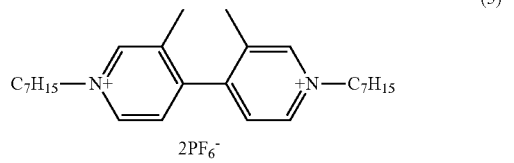

(5)

When a 3.0 V voltage was applied to the EC element of this comparative example, the EC element showed the absorption originating from the reduction species of Comparative Compound 3. The wavelength of the absorption peak of originating from, the reduction species of Comparative Compound 3 was 795 nm. When a −0.5 V voltage was further applied, a colored, state was held. More specifically, in Comparative Compound 3, the electrochemical redox reaction was irreversible.

Example 7

Durable Stability of Redox Cycle

In this example, the organic compound of each Example described above was measured for durable stability. The durable stability was measured using glassy carbon for a working electrode, platinum for a counter electrode, and silver for a reference electrode and using a solution, in which each organic compound was dissolved. The solution in which each organic compound was dissolved is a solution, in which each organic compound was dissolved in a propylene carbonate solution (0.1 mol/L) of tetrabutylammonium hexafluorophosphate as a supporting electrolyte so that the concentration was $5.0 \times 10^{-4}$ mol/L. To the solution, a rectangular wave potential containing a constant potential reduction at a reduction potential (vs. Ag/Ag$^+$)/3 seconds and a constant potential oxidation at 0 V (vs. Ag/Ag$^+$)/3 seconds of each organic compound was repeatedly applied by 30000 times. Table 1 shows the changes in the reduction peak current amount in CV measurement before the 30000 applications of the rectangular wave potential (before a redox cycle) and after the 30000 applications of the rectangular wave potential (after a redox cycle). Herein, the reduction peak current change rate is one obtained by adding the change amount from the initial current amount, which was set to 100%, to the initial current amount.

TABLE 1

| Compound | Reduction peak current amount change rate in CV measurement before and after 3000 redox cycles (%) |
| --- | --- |
| Exemplary Compound A-6 | 99% |
| Exemplary Compound B-3 | 100% |
| Exemplary Compound B-8 | 100% |
| Exemplary Compound D-1 | 90% |
| Comparative Compound 1 | 0% |

As shown in Table 1, it is understood that the organic compounds represented by General Formula (1) have a high reduction peak current change rate and have a small current amount change even after the redox cycle. Therefore, it can be said that the organic compounds represented by General Formula (1) are compounds excellent in durable stability of the redox cycle. In particular, the compounds in which $X_1$ and $X_2$ each are an aryl group or an alkyl group among the organic compounds represented by General Formula (1) shows the reduction peak current change rate of a value close to 100% and have particularly high durable stability. In Comparative Compound 1, the reduction peak current change rate was 0% and the redox reaction was irreversible.

Example 8

Synthesis of Exemplary Compound B-7

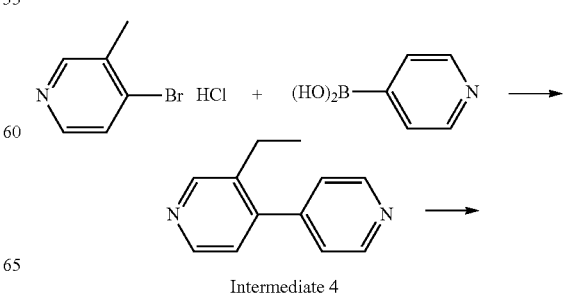

Intermediate 4

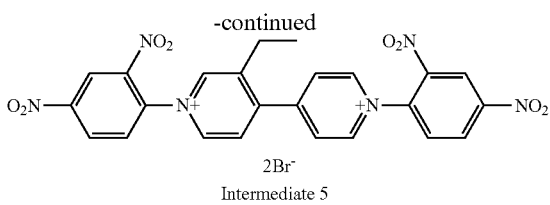

2Br⁻

Intermediate 5

With respect to Exemplary Compound B-7, an intermediate 4 was synthesized by the same synthesis method as that of Example 1, except changing the 3-methyl-4-chloropyridine hydrochloride as the raw material to 3-ethyl-4-bromopyridine hydrochloride in the synthesis of the intermediate 2 of Example 1. Furthermore, an intermediate 5 was synthesized by the same synthesis method, except changing the intermediate 2 as the raw material to the intermediate 4 in the synthesis of the intermediate 3 of Example 3.

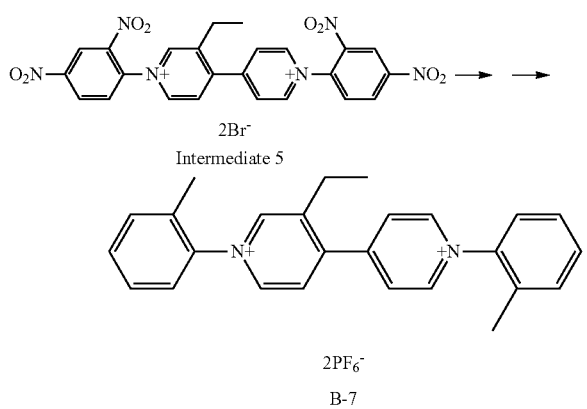

In a reaction container, the intermediate 5 (339 mg, 0.5 mmol), o-toluidine (536 mg, 5 mmol), and ethanol (10 ml) were charged, and then stirred under heating and refluxing for 8 hours. After the completion of a reaction, the ethanol was vacuum-removed, and then ethyl acetate was added to deposit a precipitate. Filtering was performed, the obtained crystal was dissolved in water, and then an aqueous solution in which potassium hexafluorophosphate (1 g) was dissolved was added dropwise. Then, after stirred at room temperature for 3 hours, the deposited crystal was filtered, and then washed with isopropyl alcohol to give 256 mg (Yield: 78%) of Exemplary Compound B-7.

The structure of Exemplary Compound B-7 was confirmed by NMR measurement.

$^1$H NMR (CD$_3$CN, 500 MHz) σ (ppm): 8.99 (d, 2H), 8.88 (s, 1H), 8.81 (d, 1H), 8.29 (d, 2H), 8.12 (d, 1H), 7.72-7.66 (m, 2H), 7.63-7.52 (m, 6H), 2.90 (m, 2H), 2.27 (s, 3H), 2.25 (s, 3H), 1.26 (t, 3H)

Example 9

Synthesis of Exemplary Compound B-9

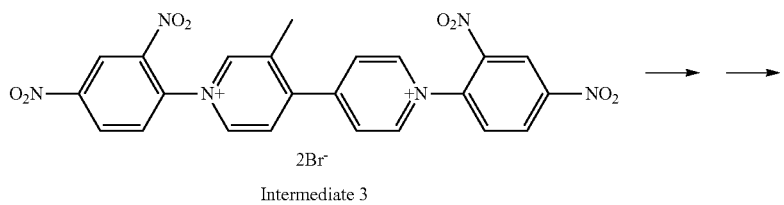

Intermediate 3

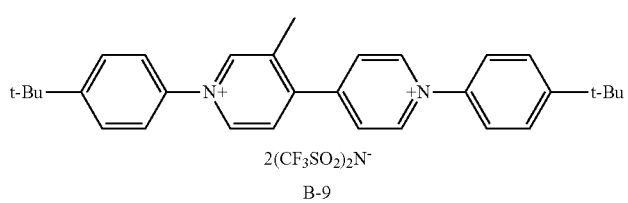

B-9

Exemplary Compound B-9 was synthesized from the intermediate 3. The intermediate 3 (332 mg, 0.5 mmol), 4-tert-butylaniline (229 mg, 1.5 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which bis(trifluoromethanesulfonyl)imidelithium (1 g) was dissolved was added dropwise, the resultant substance was stirred at room temperature for 3 hours, and then the deposited crystal was filtered. The obtained crystal was recrystallized with ethyl alcohol to give 424 mg (Yield: 85%) of Exemplary Compound B-9.

The structure of Exemplary Compound B-9 was confirmed by NMR measurement.

$^1$H NMR (CD$_3$CN, 500 MHz) σ (ppm): 9.13 (d, 2H), 9.05 (s, 1H), 8.97 (d, 1H), 8.28 (d, 2H), 8.13 (d, 1H), 7.69-7.64 (m, 4H), 7.62-7.57 (m, 4H), 2.56 (s, 3H), 1.42 (s, 9H), 1.41 (s, 9H)

Example 10

Synthesis of Exemplary Compound B-11

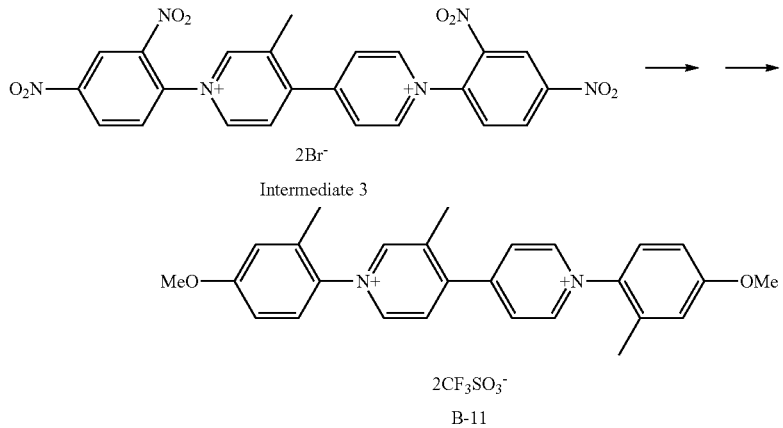

Exemplary Compound B-11 was synthesized from the intermediate 3. The intermediate 3 (332 mg, 0.5 mmol), 2-methyl-4-methoxyaniline (412 mg, 3 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which sodium trifluoromethylsulfonate (1 g) was dissolved was added dropwise, the resultant substance was stirred at room temperature for 3 hours, and then the deposited crystal was filtered. The obtained crystal was recrystallized with isopropyl alcohol to give 274 mg (Yield: 77%) of Exemplary Compound B-11.

The structure of Exemplary Compound B-11 was confirmed by NMR measurement.

$^1$H NMR (CD$_3$CN, 500 MHz) σ (ppm): 9.00 (d, 2H), 8.89 (s, 1H), 8.84 (d, 1H), 8.26 (d, 2H), 8.11 (d, 1H), 7.48 (m, 2H), 7.24 (m, 2H), 7.10 (m, 2H), 3.91 (s, 3H), 3.90 (s, 3H), 2.53 (s, 3H), 2.51 (s, 3H), 2.50 (s, 3H)

Example 11

Synthesis of Exemplary Compound B-5

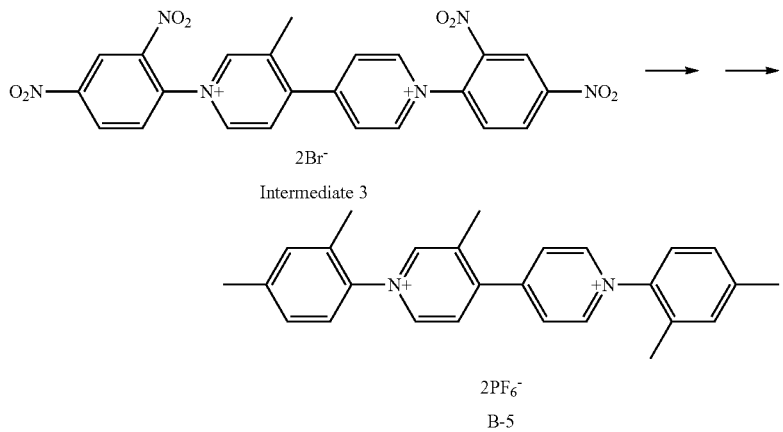

Exemplary Compound B-5 was synthesized from the intermediate 3. The intermediate 3 (332 mg, 0.5 mmol), 2,4-dimethylaniline (364 mg, 3 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which potassium hexafluorophosphate (1 g) was dissolved was added dropwise, the resultant substance was stirred at room temperature for 3 hours, and then the deposited crystal was filtered. The obtained crystal was recrystallized with isopropyl alcohol to give 282 mg (Yield: 84%) of Exemplary Compound B-5.

The structure of Exemplary Compound B-5 was confirmed by NMR measurement.

$^1$H NMR (CD$_3$CN, 500 MHz) σ (ppm): 9.00 (d, 2H), 8.85 (s, 1H), 8.80 (d, 1H), 8.29 (d, 2H), 8.13 (d, 1H), 7.48-7.34 (m, 6H), 2.55 (s, 3H), 2.48 (s, 3H), 2.47 (s, 3H), 2.22 (s, 3H), 2.20 (s, 3H)

Example 12

Synthesis of Exemplary Compound B-6

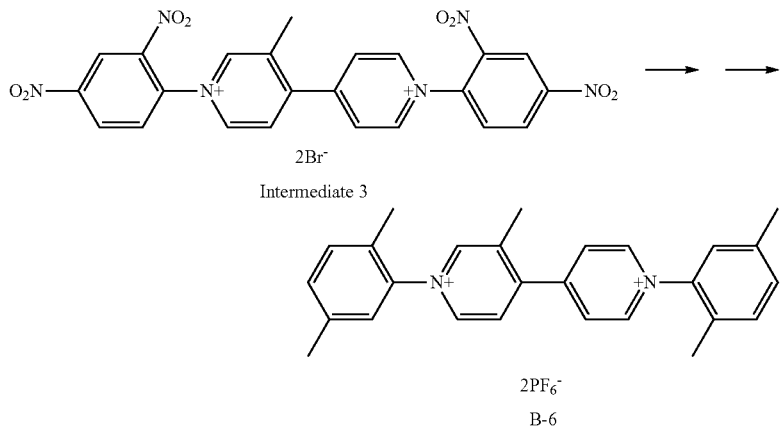

Exemplary Compound B-6 was synthesized from the intermediate 3. The intermediate 3 (332 mg, 0.5 mmol), 2,5-dimethylaniline (364 mg, 3 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which potassium hexafluorophosphate (1 g) was dissolved was added dropwise, the resultant substance was stirred at room temperature for 3 hours, and then the deposited crystal was filtered. The obtained crystal was recrystallized with isopropyl alcohol to give 285 mg (Yield: 85%) of Exemplary Compound B-6.

The structure of Exemplary Compound B-6 was confirmed by NMR measurement.

$^1$H NMR (CD$_3$CN, 500 MHz) σ (ppm): 8.97 (d, 2H), 8.85 (s, 1H), 8.79 (d, 1H), 8.31 (d, 2H), 8.15 (d, 1H), 7.54-7.45 (m, 4H), 7.39 (s, 1H), 7.34 (s, 1H), 2.56 (s, 3H), 2.46 (s, 3H), 2.45 (s, 3H), 2.22 (s, 3H), 2.20 (s, 3H)

Example 13

Synthesis of Exemplary Compound B-12

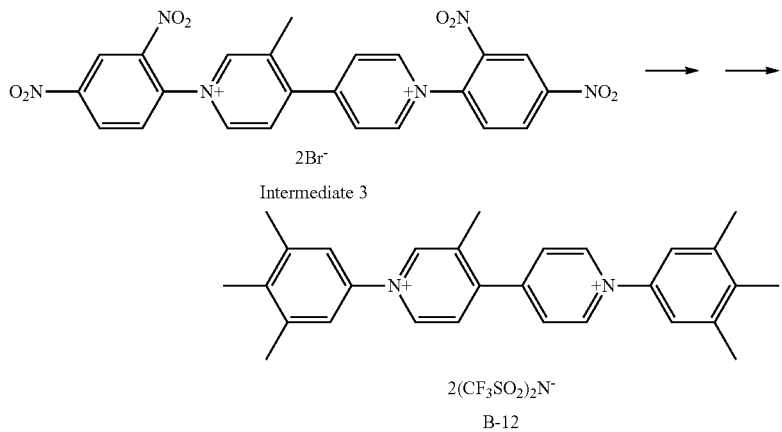

Exemplary Compound B-12 was synthesized from the intermediate 3. The intermediate 3 (332 mg, 0.5 mmol), 3,4,5-trimethylaniline (203 mg, 1.5 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which bis(trifluoromethanesulfonyl) imidelithium (1 g) was dissolved was added dropwise, the resultant substance was stirred at room temperature for 3 hours, and then the deposited crystal was filtered. The obtained crystal was recrystallized with isopropyl alcohol to give 426 mg (Yield: 88%) of Exemplary Compound B-12.

The structure of Exemplary Compound B-12 was confirmed by NMR measurement.

$^1$H NMR (CD$_3$CN, 500 MHz) σ (ppm): 9.09 (d, 2H), 9.01 (s, 1H), 8.93 (d, 1H), 8.25 (d, 2H), 8.10 (d, 1H), 7.43 (s, 4H), 2.56 (s, 3H), 2.46 (s, 6H), 2.45 (s, 6H), 2.34 (s, 3H), 2.33 (s, 3H)

Example 14

Synthesis of Exemplary Compound B-14

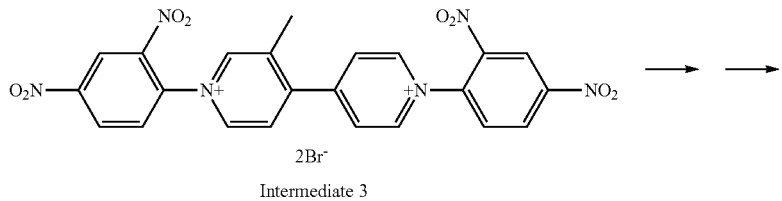

Intermediate 3

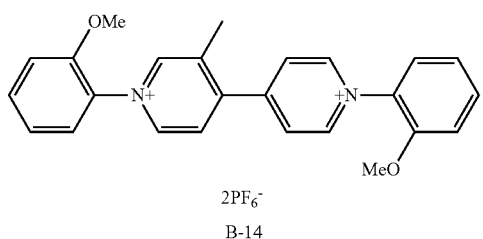

B-14

Exemplary Compound B-14 was synthesized from the intermediate 3. The intermediate 3 (332 mg, 0.5 mmol), 2-methoxyaniline (370 mg, 3 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which potassium hexafluorophosphate (1 g) was dissolved was added, dropwise, the resultant substance was stirred at room temperature for 3 hours, and then the deposited crystal was filtered. The obtained crystal was recrystallized with isopropyl alcohol to give 270 mg (Yield: 80%) of Exemplary Compound B-14.

The structure of Exemplary Compound B-14 was confirmed by NMR measurement.

$^1$H NMR (CD$_3$CN, 500 MHz) σ (ppm): 9.02 (d, 2H), 8.91 (s, 1H), 8.86 (d, 1H), 8.28 (d, 2H), 8.13 (d, 1H), 7.75 (m, 2H), 7.62 (m, 2H), 7.40 (m, 2H), 7.30 (m, 2H), 3.93 (s, 3H), 3.92 (s, 3H), 2.54 (s, 3H)

Example 15

Synthesis of Exemplary Compound B-15

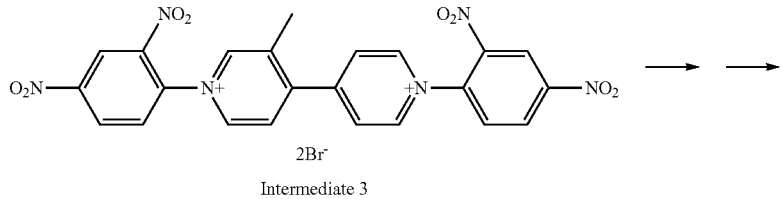

Intermediate 3

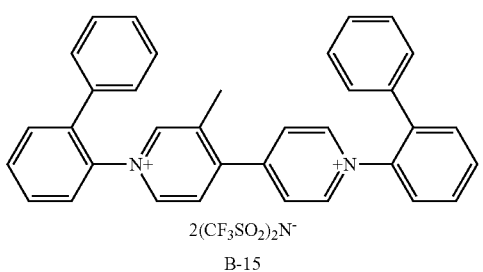

B-15

Exemplary Compound B-15 was synthesized from the intermediate 3. The intermediate 3 (332 mg, 0.5 mmol), 2-aminobiphenyl (508 mg, 3 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which bis(trifluoromethanesulfonyl)imidelithium (1 g) was dissolved was added dropwise, the resultant substance was stirred at room temperature for 3 hours, and then the deposited crystal was filtered. The obtained crystal was recrystallized with acetonitrile/isopropyl alcohol to give 467 mg (Yield: 90%) of Exemplary Compound B-15.

The structure of Exemplary Compound B-15 was confirmed by NMR measurement.

$^1$H NMR (CD$_3$CN, 500 MHz) σ (ppm): 8.87 (m, 3H), 8.62 (d, 1H), 8.01 (d, 2H), 7.87 (m, 2H), 7.83-7.68 (m, 7H), 7.38 (m, 6H), 7.19 (m, 4H), 2.30 (s, 3H)

Example 16

Synthesis of Exemplary Compound B-16

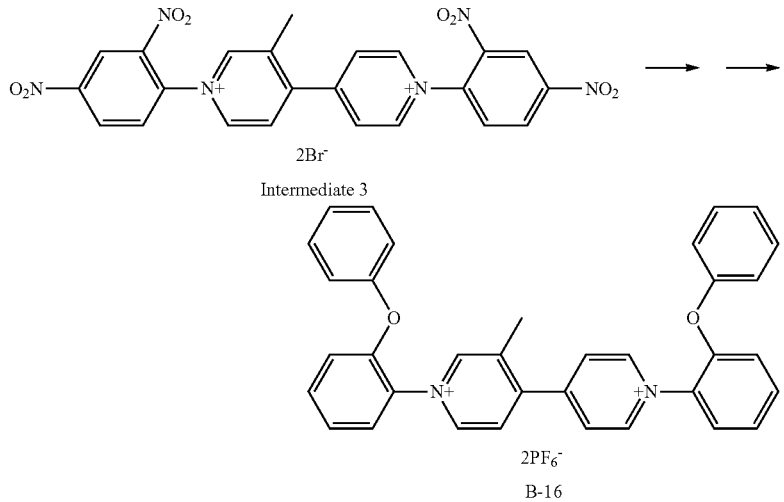

Exemplary Compound B-16 was synthesized from the intermediate 3. The intermediate 3 (332 mg, 0.5 mmol), 2-phenoxyaniline (556 mg, 3 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which potassium hexafluorophosphate (1 g) was dissolved was added dropwise, the resultant substance was stirred at room temperature for 3 hours, and then the deposited crystal was filtered. The obtained crystal was recrystallized with isopropyl alcohol to give 323 mg (Yield: 81%) of Exemplary Compound B-16.

The structure of Exemplary Compound B-16 was confirmed by NMR measurement.

$^1$H NMR (CD$_3$CN, 500 MHz) σ (ppm): 9.13 (d, 2H), 9.01 (s, 1H), 8.97 (d, 1H), 8.25 (d, 2H), 8.09 (d, 1H), 7.78-7.64 (m, 4H), 7.45 (m, 6H), 7.28 (m, 2H), 7.14 (m, 6H), 3.93 (s, 3H), 3.92 (s, 3H), 2.50 (s, 3H)

Example 17

Synthesis of Exemplary Compound B-17

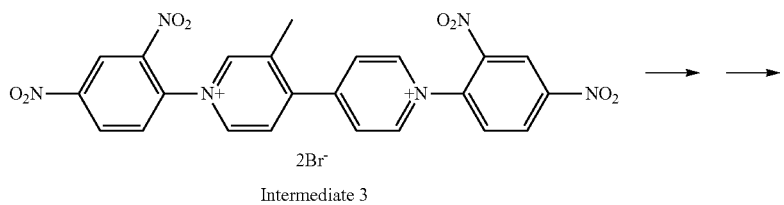

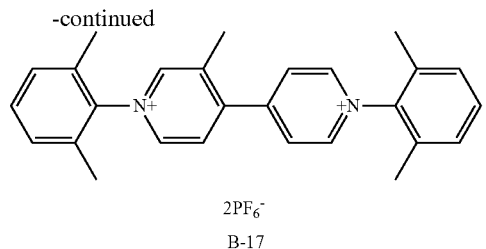

2PF₆⁻

B-17

Exemplary Compound B-17 was synthesized from the intermediate 3. The intermediate 3 (332 mg, 0.5 mmol), 2,6-dimethylaniline (606 mg, 5 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which potassium hexafluorophosphate (1 g) was dissolved was added dropwise, the resultant substance was stirred at room temperature for 3 hours, and then the deposited crystal was filtered. The obtained crystal was recrystallized with isopropyl alcohol to give 228 mg (Yield: 68%) of Exemplary Compound B-17.

The structure of Exemplary Compound B-17 was confirmed by NMR measurement.

$^1$H NMR (CD$_3$CN, 500 MHz) σ (ppm): 8.96 (d, 2H), 8.81 (s, 1H), 8.77 (d, 1H), 8.41 (d, 2H), 8.25 (d, 1H), 7.57 (m, 2H), 7.44 (m, 4H), 7.28 (m, 2H), 2.57 (s, 3H), 2.13 (s, 3H), 2.12 (s, 3H)

Example 18

Synthesis of Exemplary Compound B-20

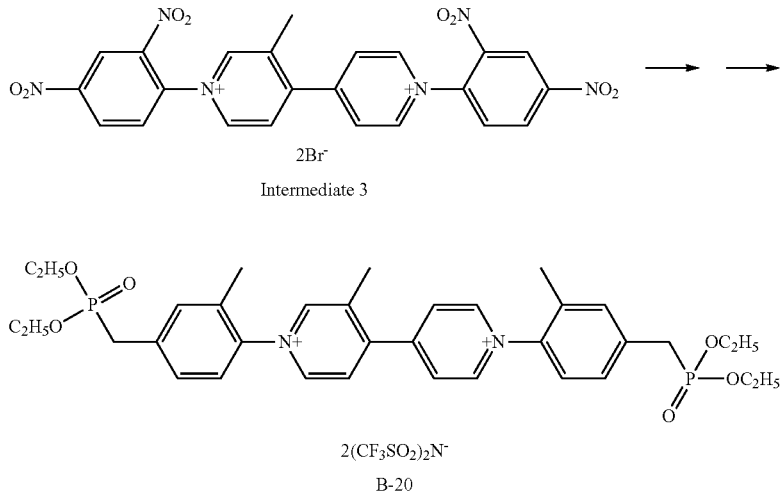

Exemplary Compound B-20 was synthesized from the intermediate 3. The intermediate 3 (332 mg, 0.5 mmol), diethyl-3-methyl-4-aminobenzylphosphonate (772 mg, 3 mmol), and ethanol (10 ml) were charged in a reaction container, and then stirred under heating and re fluxing for 8 hours. After the completion of a reaction, the ethanol was vacuum-removed, and then ethyl acetate was added to deposit a precipitate. Filtering was performed, the obtained crystal was dissolved in water, an aqueous solution in which bis(trifluoromethanesulfonyl)imidelithium (1 g) was dissolved was added dropwise, the resultant substance was stirred at room temperature for 3 hours, and then the deposited crystal was filtered. The obtained crystal was recrystallized with acetonitrile/isopropyl alcohol to give 323 mg (Yield: 81%) of Exemplary Compound B-20.

The structure of Exemplary Compound B-20 was confirmed by NMR measurement.

$^1$H NMR (CD$_3$CN, 500 MHz) σ (ppm): 9.00 (d, 2H), 8.88 (s, 1H), 8.82 (d, 1H), 8.31 (d, 2H), 8.15 (a, 1H), 7.55-7.46 (m, 6H), 4.07 (m, 8H), 3.33 (d, 2H), 3.29 (d, 2H), 2.56 (s, 3H), 2.26 (s, 3H), 2.24 (s, 3H), 1.29 (t, 12H)

Example 19

Synthesis of Exemplary Compound B-22

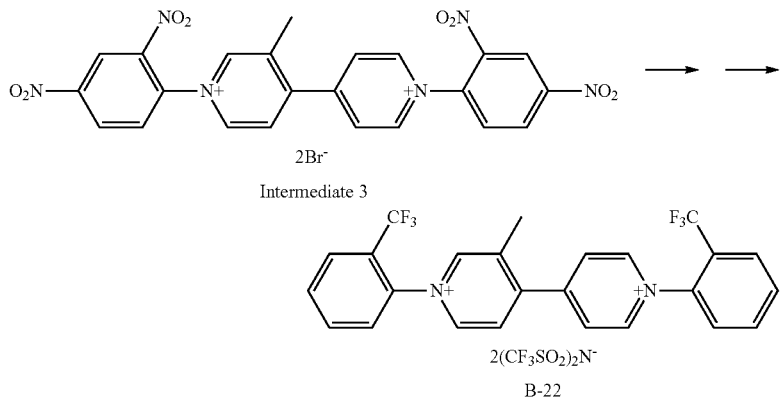

Exemplary Compound B-22 was synthesized from the intermediate 3. The intermediate 3 (332 mg, 0.5 mmol), 2-trifluoromethylaniline (483 mg, 3 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which bis(trifluoromethanesulfonyl)imidelithium (1 g) was dissolved was added dropwise, the resultant substance was stirred at room temperature for 3 hours, and then the deposited crystal was filtered. The obtained crystal was recrystallized with isopropyl alcohol to give 424 mg (Yield: 83%) of Exemplary Compound B-22.

The structure of Exemplary Compound B-22 was confirmed by NMR measurement.

$^1$H NMR (CD$_3$CN, 500 MHz) σ (ppm): 9.13 (d, 2H), 9.00 (s, 1H), 8.96 (d, 1H), 8.39 (m, 2H), 8.24 (d, 1H), 8.13 (m, 2H), 8.08-7.98 (m, 4H), 7.88 (d, 1H), 7.80 (d, 1H), 2.56 (s, 3H)

Example 20

Synthesis of Exemplary Compound B-23

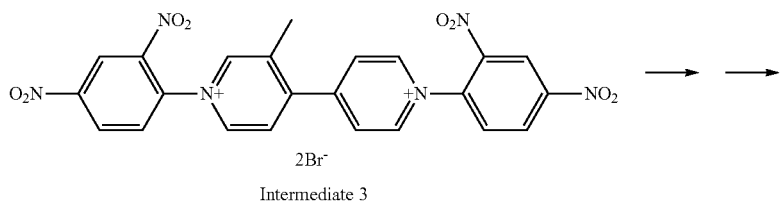

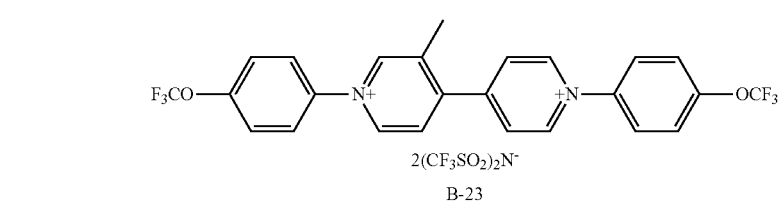

Exemplary Compound B-23 was synthesized from the intermediate 3. The intermediate 3 (332 mg, 0.5 mmol), 4-(trifluoromethoxy)aniline (266 mg, 1.5 mmol), and ethanol (10 ml) were charged in a reaction container, and then stirred under heating and refluxing for 8 hours. After the completion of a reaction, the ethanol was vacuum-removed, and then ethyl acetate was added to deposit a precipitate. Filtering was performed, the obtained crystal was dissolved in water, an aqueous solution in which bis(trifluoromethanesulfonyl)imidelithium (1 g) was dissolved was added dropwise, the resultant substance was stirred at room temperature for 3 hours, and then the deposited crystal was filtered. The obtained crystal was recrystallized with isopropyl alcohol to give 421 mg (Yield: 80%) of Exemplary Compound B-23.

The structure of Exemplary Compound B-23 was confirmed by NMR measurement.

$^1$H NMR (CD$_3$CN, 500 MHz) σ (ppm): 9.13 (d, 2H), 9.05 (s, 1H), 8.98 (d, 1H), 8.32 (d, 2H), 8.16 (d, 1H), 7.90 (m, 4H), 7.71 (d, 4H), 2.56 (s, 3H)

Example 21

Production and Evaluation of Properties of Electrochromic Element

In this example, EC elements were produced using the organic compounds represented by General Formula (1) and the properties thereof were evaluated by the same technique as that of Example 6. As the organic compounds represented by General Formula (1), Exemplary Compounds B-5, B-6, B-7, B-9, B-11, B-12, B-14, B-15, B-16, B-17, B-20, B-22, and B-23 synthesized in Examples 8 to 20 and Compound B-10 were used.

The wavelengths of the absorption peaks of the absorption originating from the reduction species in the EC-elements of this example are shown in Table 2.

TABLE 2

| Reduction species | Absorption peak wavelength |
| --- | --- |
| Exemplary Compound B-5 | 408 nm 650 nm |
| Exemplary Compound B-6 | 408 nm 650 nm |
| Exemplary Compound B-7 | 409 nm 658 nm |
| Exemplary Compound B-9 | 447 nm 703 nm |
| Exemplary Compound B-10 | 432 nm 689 nm |
| Exemplary Compound B-11 | 447 nm 703 nm |
| Exemplary Compound B-12 | 454 nm 709 nm |
| Exemplary Compound B-14 | 428 nm 689 nm |
| Exemplary Compound B-15 | 420 nm 696 nm |
| Exemplary Compound B-16 | 422 nm 689 nm |
| Exemplary Compound B-17 | 402 nm 650 nm |
| Exemplary Compound B-20 | 408 nm 650 nm |
| Exemplary Compound B-22 | 403 nm 652 nm |
| Exemplary Compound B-23 | 436 nm 709 nm |

A 3.0 V voltage was applied to the EC elements of this example, and then the EC elements showed the absorption originating from the reduction species of the organic compounds contained in the EC elements. Thereafter, when a −0.5 V voltage was further applied, all the EC elements decolored. More specifically, the EC elements of this example can reversibly change a colored state and a decolored state and has the EC property.

As described above, the organic compounds represented by General Formula (1) have the absorption peak in a wavelength band of 650 nm or more in a reduced state (colored state).

Example 22

Synthesis of Exemplary Compound H-2

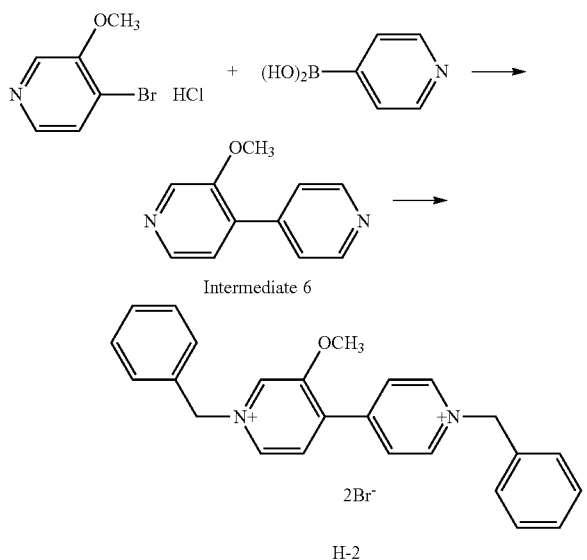

In a reaction container, 3-methoxy4-bromopyridine hydrochloride (0.81 g, 3.6 mmol), 4-pyridyl boronic acid (0.65 g, 5.3 mmol), tris(dibenzylideneacetone)dipalladium (0) (65 mg, 0.07 mmol), tricyclohexylphosphine (45 mg, 0.16 mmol), 2 g of tripotassium phosphate (n hydrate), 10 ml of dioxane, and 6 ml of water were charged, and then stirred under heating and refluxing under a nitrogen stream for 8 hours. After the completion of a reaction, the reaction liquid was condensed, and then extracted with ethyl acetate. An organic layer was washed with water, dried over magnesium sulfate, and then dried under reduced pressure. The resultant substance was purified by silica gel chromatography (Eluate: Chloroform/Methanol=10/1), and then recrystallized with diisopropyl ether to give 0.38 g (Yield: 57%) of intermediate 6.

The structure of this compound was confirmed by NMR measurement.

$^1$H NMR (CDCl$_3$, 500 MHz) σ (ppm): 8.69 (m, 2H), 8.42 (s, 1H), 8.37 (d, 1H), 7.49 (m, 2H), 7.26 (d, 1H), 3.95 (s, 3H)

In a reaction container, the intermediate 6 (186 mg, 1 mmol), benzylbromide (513 mg, 3 mmol), and 10 ml of acetonitrile were charged, and then heated and refluxed under a nitrogen stream for 8 hours. After the completion of a reaction, ethyl acetate was added dropwise to the reaction liquid, and then the obtained crystal was washed with ethyl acetate to give 423 mg (Yield: 80%) of Exemplary Compound H-2.

The structure of this compound was confirmed by NMR measurement.

$^1$H NMR (DMSO-d6, 500 MHz) σ (ppm): 9.40 (m, 3H), 9.07 (d, 1H), 8.46 (d, 2H), 8.31 (d, 1H), 7.65 (m, 2H), 7.60 (m, 2H), 7.47 (m, 6H), 5.93 (s, 2H), 5.92 (s, 2H), 4.08 (s, 3H)

Example 23

Synthesis of Exemplary Compound H-1

Exemplary Compound H-2 was dissolved in water (118 mg, 0.2 mmol). An aqueous solution in which 200 mg of potassium hexafluorophosphate was dissolved was added dropwise, and then stirred at room, temperature for 3 hours. The deposited crystal was filtered, and then successively washed with, isopropyl alcohol and diethylether to give 116 mg (Yield: 88%) of Exemplary Compound H-1.

The structure of this compound was confirmed by NMR measurement.

$^1$H NMR (CD$_3$CN, 500 MHz) σ (ppm): 8.88 (d, 2H), 8.66 (s, 1H), 8.55 (d, 1H), 8.25 (d, 2H), 8.01 (d, 1H), 8.31 (d, 1H), 7.52 (m, 10H), 5.80 (s, 2H), 5.79 (s, 2H), 4.07 (s, 3H)

Example 24

Production and Evaluation of Properties of Electrochromic Element

In this example, an EC element was produced using the organic compound represented by General Formula (1) and the properties thereof were evaluated by the same technique as that of Example 21. As the organic compound represented by General Formula (1), Exemplary Compound H-1 synthesized in Example 23 was used.

The EC element of this example immediately after the production showed a transmittance of about 80% over the entire visible light region and had high transparency.

Figure 8:
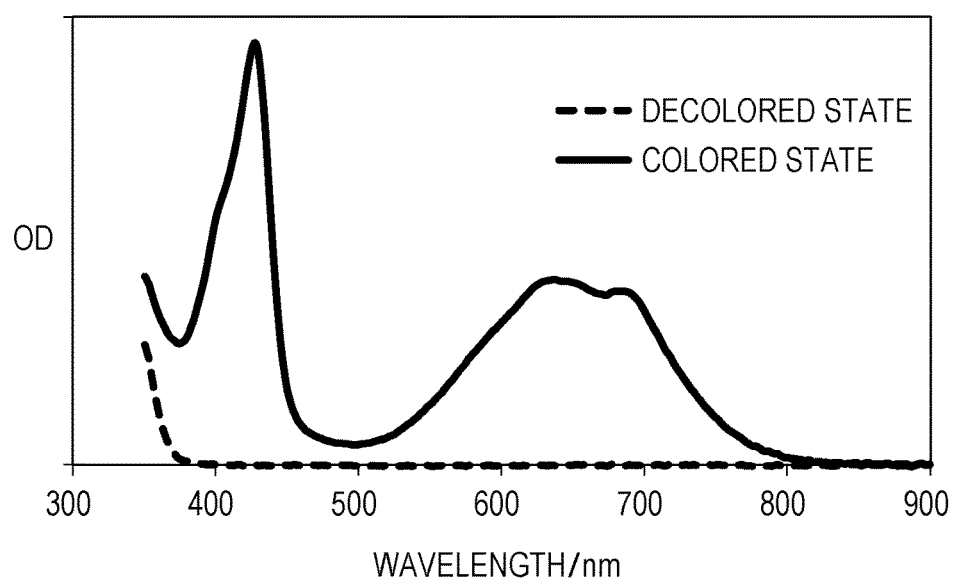
FIG. 8 is the ultraviolet visible absorption spectra in a colored state and a decolored state of Exemplary Compound H-1 according to an embodiment of the subject application.

When a 3.0 V voltage was applied to the EC element of this example, the EC element showed absorption (λmax=428 nm, 638 nm) originating from the reduction species of Exemplary Compound H-1, and the EC element was colored green. When a −0.5 V voltage was applied, the EC element decolored. FIG. 8 shows the ultraviolet visible absorption spectra of the EC element of this example. For the light-source, a DH-2000S Deuterium Halogen Light Source of Ocean Optics, Inc. was used.

In the EC element, as a result of repeating a colored state for 10 seconds and a decolored state for 10 seconds by 1000 times, no changes in the absorption spectra in a colored state and a decolored state were observed.

As described above, according to the organic compounds according to the embodiments and Examples described above, organic compounds having the absorption peak in a long wavelength band as compared with that of viologen in which no substituents are introduced into the carbon atoms of 4,4'-bipyridinium in a colored state can be provided. Moreover, according to the organic compounds according to the embodiments and Examples described above, organic compounds in which an electrochemical redox reaction reversibly progresses can be provided.

Moreover, the organic compounds according to the embodiments and Examples described above have high durable stability. Therefore, the organic compounds according to the embodiments and Examples described above can be utilized for an EC element which is required to have high durable stability.

The organic compounds according to the embodiments and Examples described above are electrochromic compounds having the EC property and can be utilized for an EC element and an optical filter, a lens unit, an imaging device, a window component, and the like containing the same.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2016-096254 filed May 12, 2016 and No. 2017-076185 filed Apr. 6, 2017, which are hereby incorporated by reference herein in their entirety.

What is claimed is:

1. An organic compound of Formula (1),

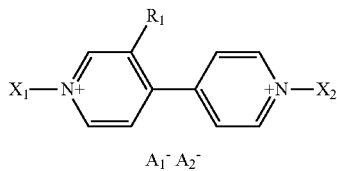

wherein, in Formula (1), $R_1$ is an alkyl group or an alkoxy group, $X_1$ and $X_2$ are each independently selected from an alkyl group which may have a substituent, an aryl group which may have a substituent, or an aralkyl group which may have a substituent, and $A_1^-$ and $A_2^-$ are each independently a monovalent anion.

2. The organic compound according to claim 1, wherein a reduction of the organic compound produces a reduced state which is colored and which reduced state has an absorption peak in a wavelength band of 630 nm or more and 750 nm or less.

3. The organic compound according to claim 1, wherein, in Formula (1), $R_1$ is an alkyl group having from 1 to 8 carbon atoms.

4. The organic compound according to claim 1, wherein, in Formula (1), $R_1$ is an alkoxy group having from 1 to 8 carbon atoms.

5. The organic compound according to claim 1, wherein, in Formula (1), $X_1$ and $X_2$ are each independently an alkyl group which may have a substituent or an aryl group which may have a substituent.

6. The organic compound according to claim 1, wherein the organic compound is an electrochromic compound a color tone of which is changed by a redox reaction.

7. The organic compound according to claim 1, wherein the $A_1^-$ and the $A_2^-$ are same anions.

8. An electrochromic compound, for use as an electrochromic element, of Formula (1),

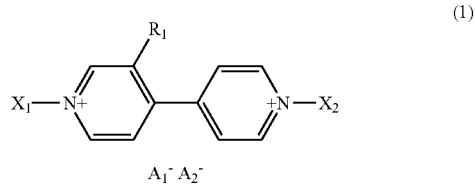

wherein, in Formula (1), $R_1$ is an alkyl group or an alkoxy group, $X_1$ and $X_2$ are each independently selected from an alkyl group which may have a substituent, an aryl group which may have a substituent, or an aralkyl group which may have a substituent, and $A_1^-$ and $A_2^-$ are each independently a monovalent anion.

9. An electrochromic element comprising:
a pair of electrodes; and
an electrochromic layer disposed between the pair of electrodes, wherein
the electrochromic layer contains the organic compound according to claim 1.

10. The electrochromic element according to claim 9, wherein the electrochromic layer further contains another kind of organic compounds that is different from the organic compound.

11. The electrochromic element according to claim 10, wherein the another kind of organic compounds is any one of a phenazine compound, ferrocene, a metallocene compound, a phenylenediamine compound, and a pyrazoline compound.

12. The electrochromic element according to claim 9, wherein the electrochromic layer is liquid having an electrolyte and the organic compound.

13. An optical filter comprising:
the electrochromic element according to claim 9; and
an active element connected to the electrochromic element.

14. The optical filter according to claim 13, wherein the active element adjusts an amount of light passing through the electrochromic element by driving the electrochromic element.

15. A lens unit comprising:
the optical filter according to claim 13; and
an imaging optical system having a plurality of lenses.

16. An imaging device comprising:
an imaging optical system having a plurality of lenses;
the optical filter according to claim 13; and
an imaging element receiving light passing through the optical filter.

17. An imaging device, to which an imaging optical system having a plurality of lenses is attachable, the imaging device comprising:
   the optical filter according to claim 13; and
   an imaging element receiving light passing through the optical filter.

18. A window component comprising:
   a pair of substrates;
   the electrochromic element according to claim 9 disposed between the pair of substrates; and
   an active element connected to the electrochromic element, wherein
   the electrochromic element adjusts an amount of light passing through the pair of substrates.

* * * * *